(12) United States Patent
Runge

(10) Patent No.: US 11,994,516 B2
(45) Date of Patent: May 28, 2024

(54) COMPOSITION, METHOD AND KIT FOR PATHOLOGY

(71) Applicant: Richard Runge, Omaha, NE (US)

(72) Inventor: Richard Runge, Omaha, NE (US)

( * ) Notice: Subject to any disclaimer, the term of this patent is extended or adjusted under 35 U.S.C. 154(b) by 439 days.

(21) Appl. No.: 16/907,909

(22) Filed: Jun. 22, 2020

(65) Prior Publication Data
US 2021/0063385 A1    Mar. 4, 2021

Related U.S. Application Data

(63) Continuation of application No. 15/553,907, filed as application No. PCT/US2016/019720 on Feb. 26, 2016, now abandoned.

(60) Provisional application No. 62/121,601, filed on Feb. 27, 2015.

(51) Int. Cl.
| | |
|---|---|
| *G01N 33/532* | (2006.01) |
| *C07K 16/24* | (2006.01) |
| *C07K 16/28* | (2006.01) |
| *G01N 33/569* | (2006.01) |
| *G01N 33/58* | (2006.01) |

(52) U.S. Cl.
CPC ........... *G01N 33/532* (2013.01); *C07K 16/24* (2013.01); *C07K 16/2896* (2013.01); *G01N 33/569* (2013.01); *G01N 33/58* (2013.01)

(58) Field of Classification Search
CPC .. C07K 16/24; C07K 16/2896; G01N 33/532; G01N 33/569; G01N 33/58
See application file for complete search history.

(56) References Cited

U.S. PATENT DOCUMENTS

| | | | |
|---|---|---|---|
| 4,208,479 A | 6/1980 | Zuk et al. | |
| 2014/0037659 A1* | 2/2014 | Baniyash | G01N 33/569 435/7.1 |

FOREIGN PATENT DOCUMENTS

| | | |
|---|---|---|
| WO | 2014029012 A1 | 2/2014 |

OTHER PUBLICATIONS

Shim et al., "Prevalence of Monoclonal B-Cell Lymphocytosis: A Systematic Review," Cytometry B Clin Cytom., 2010, vol. 78 (Suppl 1), pp. S10-S18.*
Dagliks et al., "The immunoglobulin gene repertoire of low-count chronic lymphocytic leukemia (CLL)-like monoclonal B lymphocytosis is different from CLL: diagnostic implications for clinical monitoring," Blood, 2009, vol. 114, No. 1, pp. 26-32.*
Colovai, A. I. et al., Flow cytometric analysis of normal and reactive spleen, Modern Pathology, 2004, vol. 17, pp. 918-927.
International Search Report and Written Opinion for International Application No. PCT/US2016/19720, Korean Intellectual patent Office, Korea, dated May 17, 2016.
International Preliminary Report on Patentability for Application No. PCT/US2016/019720 dated Aug. 29, 2017.
Magro C., et al., "Automated Kappa and Lambda Light Chain mRNA Expression for the Assessment of B-cell Clonality in Cutaneous B-cell Infiltrates: Its Utility and Diagnostic Application," Journal of Cutaneous Pathology, Sep. 2003, vol. 30 (8), pp. 504-511.
Vandermeer, W. et al., 'The divergent morphological classification of variant lymphocytes in blood smears' , Journal of Clinical Pathology, 2007, vol. 60, pp. 838-839.
Wu G.P., et al., "Immunocytochemical Panel for Distinguishing Carcinoma Cells From Reactive Mesothelial Cells in Pleural Effusions," Cytopathology, Aug. 2008, vol. 19 (4), pp. 212-217.
Zhu M., et al., "Combining Magnetic Nanoparticle With Biotinylated Nanobodies for Rapid and Sensitive Detection of Influenza H3N2," Nanoscale Research Letters, Sep. 2014, vol. 9 (1), pp. 528 (1-10).
"Immune cell guide. Human and mouse antigens," retrieved from https://assets.thermofisher.com/TFS-Assets/LSG/brochures/immune-cell-guide.pdf on Dec. 17, 2019.
Ramos-Vara et al., "When tissue antigens and antibodies get along: revisiting the technical aspects of immunohistochemistry-the red, brown and blue technique". Veterinary Pathology, 2014, vol. 51, No. 1, pp. 42-87.
Chalmers et al., "Quantification of non-specific binding of magnetic mirco- and nanoparticles using cell tracking velocimetry: Implication for magnetic cell separation and detection," Biotechnol. Bioeng., 2010, vol. 105, No. 6, pp. 1078-1093.
A printout "MilliporeSigma Calbiochem Biotin-X-NHS, Water-Soluble" retrieved from https://www.fisherci.com/shop/products/biotin-x-nhs-water-soluble/201318950mg# on Dec. 17, 2019.

* cited by examiner

*Primary Examiner* — Galina M. Yakovleva
(74) *Attorney, Agent, or Firm* — Mallory M. Henninger; Advent, LLP

(57) ABSTRACT

Disclosed herein are embodiments of compositions, methods and kits that describe ancillary reagent constructs for simultaneous immunological and morphological investigation of pathology specimens. The kits include reagents, possibly organized in panels, which give the pathologist additional confidence in making a diagnosis based on the morphology of a cell. Reagents can be used or selected to identify specific antigens or a class of antigens. The reagents further comprise detection agents, which are visible under standard microscopy in the presence of standard stains. The reagents, used on their own or as part of a kit, make possible immunological analysis simultaneously with pathology performed in the presence of standard stains.

7 Claims, 21 Drawing Sheets

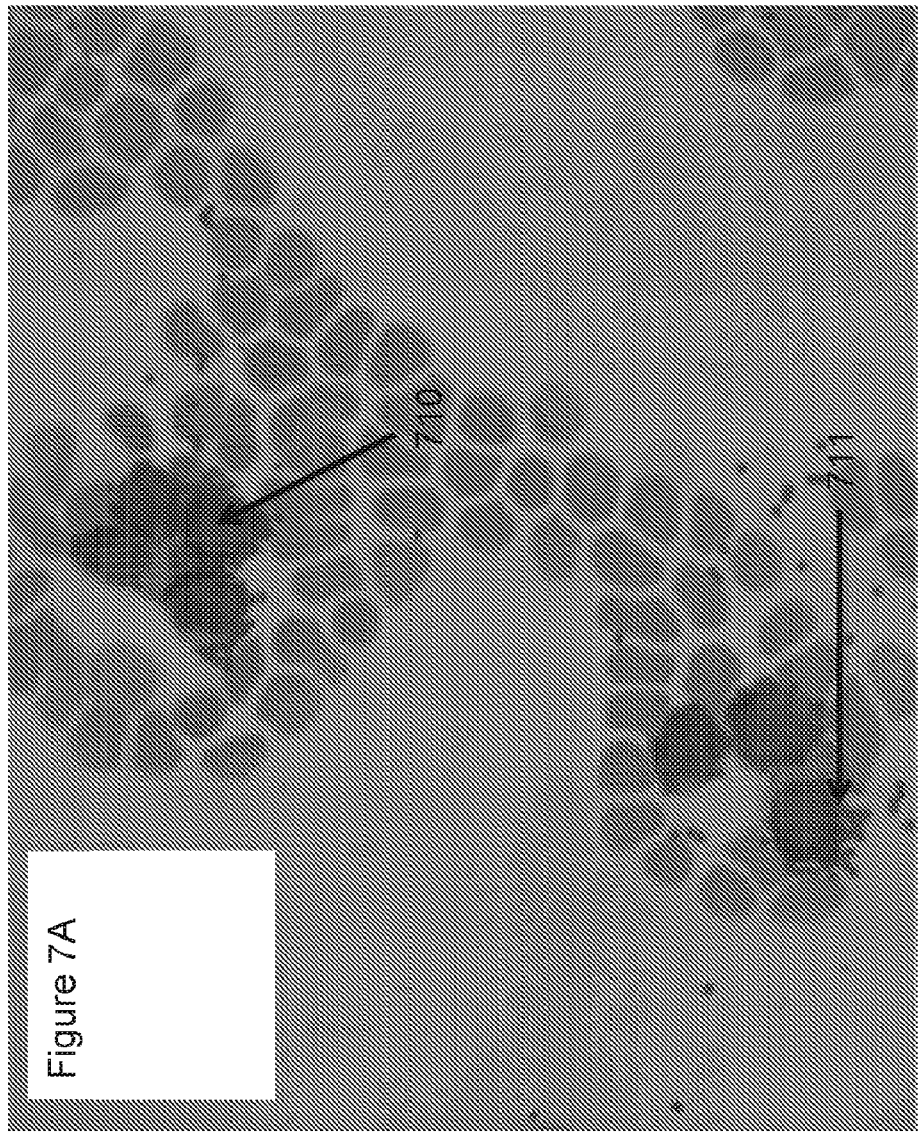

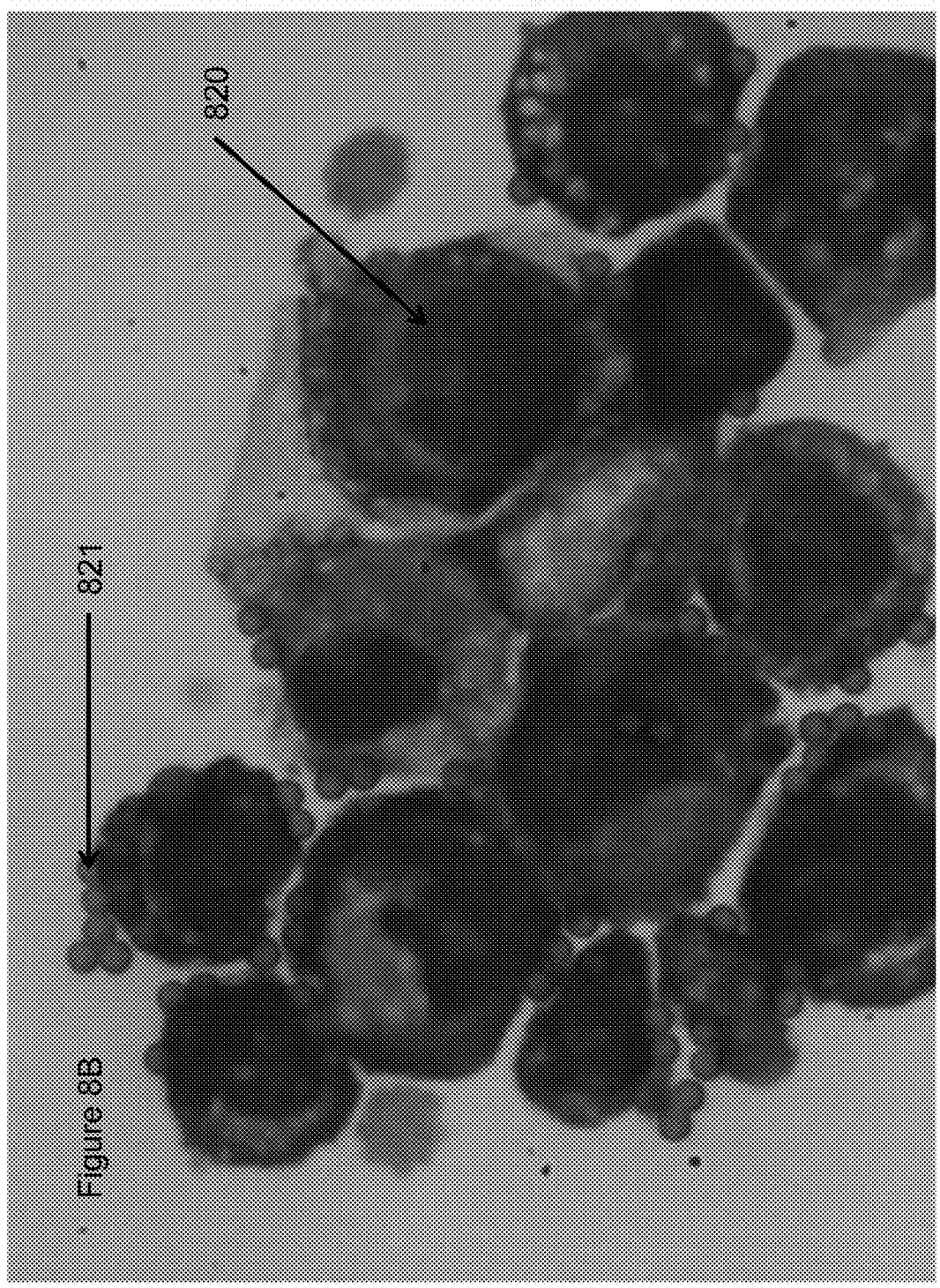

COMPOSITION, METHOD AND KIT FOR PATHOLOGY

CROSS-REFERENCE TO RELATED APPLICATIONS

This application is a continuation under 35 U.S.C. § 120 of U.S. patent application Ser. No. 15/553,907, filed Aug. 25, 2017, and titled "COMPOSITION, METHOD AND KIT FOR PATHOLOGY," which in turn claims priority to U.S. Provisional Application No. 62/121,601, filed on Feb. 27, 2015 and titled "Method, construct and system kit for pathology." U.S. patent application Ser. No. 15/553,907 and U.S. Provisional Application Ser. No. 62/121,601 are each herein incorporated by reference in its entirety.

TECHNICAL FIELD

The present disclosure relates generally to reagents, methods and kits for pathology.

BACKGROUND

Every diagnosis that a pathologist makes begins and ends with anatomical pathology. Pathologists examine patient samples to diagnose diseases. Their main tool is light microscopy, which evaluates specimens stained with standard stains. Pathology generally comes in two forms: histopathology and cytopathology.

The examination of a specimen taken from a patient via biopsy or as a surgical specimen is called histopathology. A histopathological specimen is usually processed into histological sections, stained (typically using standard stains) placed on a slide and examined under light microscopy.

In contrast, cytopathology examines free, individual cells or tissue fragments. Specimens in cytopathology are often isolated from tissues with liquid matrix, such as blood or processed specimens comprising suspended individual cells in a liquid. The laboratory prepares the specimen by smearing it onto a glass slide, which is then evaluated utilizing light microscopy. Collectively, histopathology and cytopathology are anatomical pathology; the pathologist makes a diagnosis based on the anatomical state of the specimen.

Anatomical pathology relies on staining agents to permit the morphological features of a sample to be readily observed under a light microscope. A pathologist, after examining the stained sample, makes a qualitative determination if the cell (cytopathology) or tissue (histopathology) is abnormal. The examination is anatomical; the pathologist evaluates the morphological features of the specimen to assess if it is normal or abnormal. Abnormality indicates the presence of disease or a biological state of interest.

Cytopathology involves the observation of samples of a patient's cells under a microscope to identify a wide variety of potential morphological abnormalities. Pathologists look at cell and nuclear shape, cell size or staining behavior to determine if a cell is abnormal. The evaluation is inherently subjective. The diagnostic results are often not highly sensitive or reproducible, especially at the early stages of cancer when cell morphology has not substantially diverged from non-neoplastic cells.

To assist in making a diagnosis, pathologists often use ancillary techniques, like cell blocks, flow cytometry and immunoperxidase. Ancillary techniques provide additional data but the final, legal basis of the diagnosis is the pathologist's interpretive evaluation of the specimen. The process by which anatomical pathologists diagnose disease remains largely unchanged over the last 100 years.

Flow cytometry has become a critical ancillary technique in cytopathology. The advent of new fluorochrome-conjugated antibodies has made the technique very sensitive for cytopathology. As a result, flow cytometry is often the last word in specimens with borderline morphology. All ancillary techniques delay the diagnosis but flow cytometry requires specialized equipment and personnel, usually outside of the clinical laboratory, which delays the final pathology report.

Flow cytometry is also expensive. Reliable results require specialized equipment and expensive reagents. The equipment is expensive to maintain and requires specific validation using specialized standards. Technicians trained to conduct flow cytometry are highly trained and add substantially to the cost of its clinical utilization.

All ancillary techniques, including flow cytometry, also cost time. The equipment and the capability to perform ancillary techniques are rarely at the anatomical laboratory. Samples need to be sent to an external lab, processed and reported back to the primary clinical lab. Their use can take days or weeks.

Ancillary techniques are also wholly external to anatomical pathology and the results must be interpreted separately. There is no way for a pathologist to look at a cell with questionable morphology and consider if an antigen is on the surface of the cell. She must instead integrate the anatomical data and the immunological results from the ancillary technique independently.

Anatomical pathology is the critical tool for the early diagnosis of a variety of disorders. The same aspects that make it subjective and difficult to reproduce also make it flexible and capable of reporting a wide array of disorders. When used appropriately in conjunction with ancillary techniques it is a powerful tool for the diagnosis of a variety of disorders.

BRIEF DESCRIPTION OF THE DRAWINGS

The illustrations of various embodiments of the invention are made by way of example and not intended to limit the scope of the invention.

FIGS. 7a through 7e are photomicrographs of specimens evaluated using embodiments of the hematology/pathology ancillary kit.

FIGS. 8a through 8f are photomicrographs of specimens evaluated using embodiments of the body fluid ancillary kit.

DETAILED DESCRIPTION

Ancillary Reagent Construct

Figure 1:
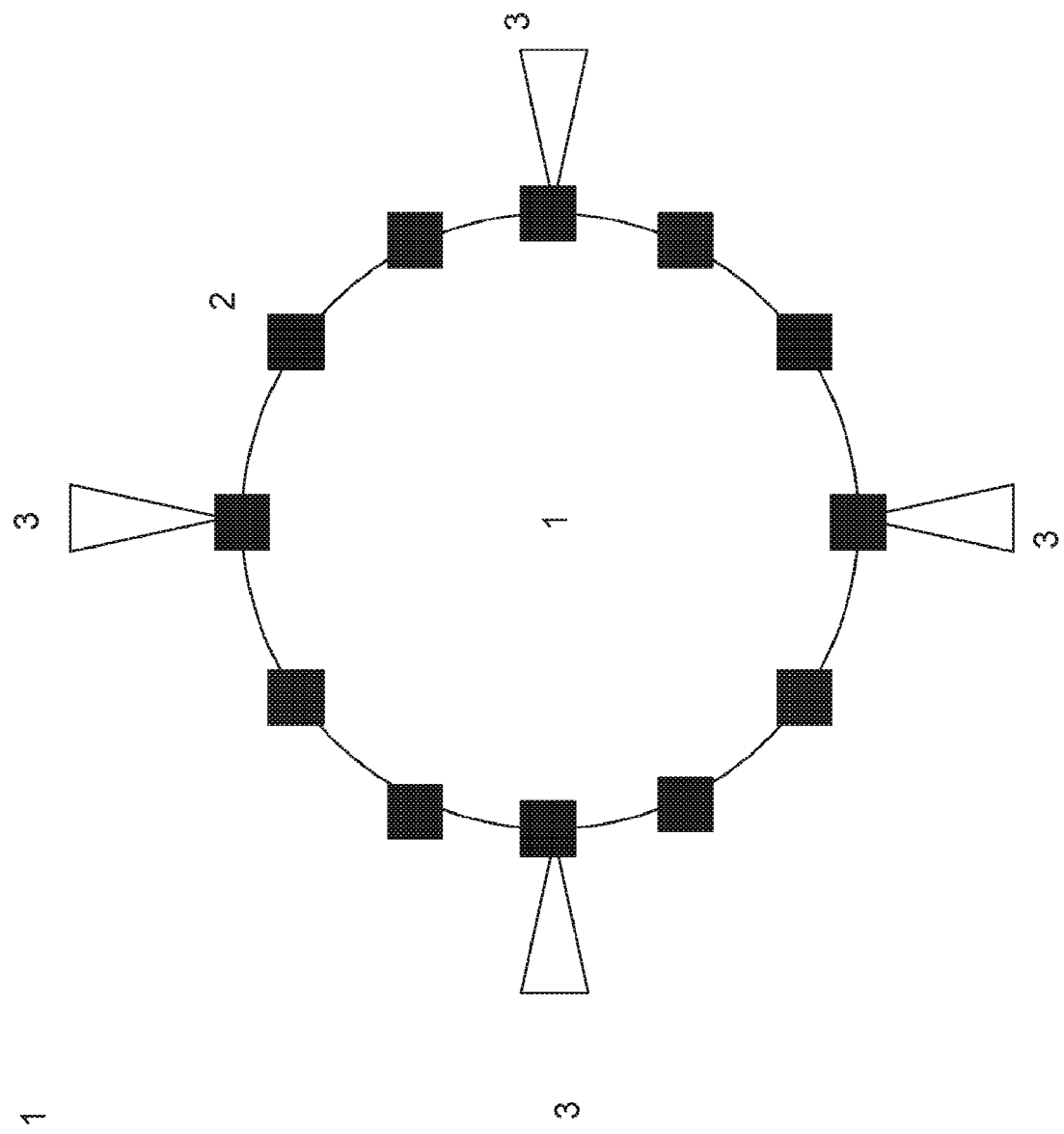
FIG. 1 is a diagram illustrating the structure, although not to scale, of the ancillary reagent construct.

Disclosed herein are embodiments of compositions, methods and kits that describe ancillary reagent constructs for simultaneous immunological and morphological investigation of pathology specimens. For example, in some embodiments, a kit contains one or more ancillary reagent constructs. Each reagent is a detection agent conjugated to one or more antibodies. The antibodies are selected to bind antigens associated with a disease or biological state of interest and conjugated to a detection agent that is visible under standard light microscopy and compatible with standard stains. The reagent is administered to pathology specimens and visualized in the course of ordinary anatomical pathology: making possible simultaneous immunological and anatomical investigation.

Simultaneous immunological and morphological investigation is currently impossible. In all pathology, anatomical investigation is done using standard stains and light microscopy. Ancillary techniques cannot be used simultaneously with anatomical pathology. Flow cytometry, for example, utilizes wholly different technology and immunoperoxidase and cell blocks are incompatible with standard stains.

Current practice treats and considers anatomical pathology as a separate investigation than ancillary techniques. The subjective, morphological interpretation of cells, practiced much the same for a century, is a first analysis. Ancillary techniques are performed afterwards, when the morphological analysis is less than conclusive. The integration of morphological and immunological investigation, in a single examination, is currently beyond the imagination of modern pathology.

The following detailed description makes reference to the accompanying drawings that form a part hereof. Numerals designate like parts of the drawings that illustrate embodiments of the invention contemplated in the practice of the invention. Other embodiments may be utilized. Changes to the component elements of the invention do not depart from the scope of the present disclosure. This detailed description is not to be taken in a limiting sense.

Various methods or processes may be presented as a series of steps that are shown in a manner that is most helpful in understanding the present invention. The order of the steps does not necessarily imply any dependent relationship. The steps of the method may be performed in a different order or equivalent steps, as known by one skilled in the art, may reasonably be substituted.

Phrases that reference an "embodiment", that refer to at least one exemplary means of practicing the invention which may be the same as, different than, wholly comprising or wholly different than another means of practicing the invention. The terms "comprising," "including," "having," and the like, as used with respect to embodiments of the present disclosure, are synonymous. As used herein, the term "antibody" can refer to any protein capable of counteracting a specific antigen and further refers to immunoglobulin molecules and other similar molecules that mediate the selective binding of an antigen. "Specimen" refers to any part of a mammal that is taken to a laboratory for further analysis. In particular, specimen refers to a mammalian tissue sample in a liquid matrix, which contains free cells, which can be visualized, in the presence of standard stains, under light microscopy. Liquid matrix can include solid samples of cells, which will be physically disrupted to create suspensions of individual cells as well. Similarly, a patient is the mammal from which the specimen comes. "Cytology Specimen" means any body fluid, fine needle aspirate, peripheral blood, bone marrow, lymph node biopsy or other specimen ordinarily evaluated by cytopathology, "Pathology" may refer broadly to histopathology, cytopathology and related evaluation of tissues for characteristics, morphological or otherwise, that indicate the presence of disease or a biological state of interest "Cytopathology" may refer to the evaluation of free cells for characteristics, morphological or otherwise, consistent with disease or a biological state of interest. "Ancillary technique" refers to any method that contributes to the evaluation pathology specimen that is ancillary to the morphological analysis that is conducted by, supervised by or otherwise the responsibility of a pathologist. The anatomical pathologist responsible for the diagnosis made from the specimen can perform an ancillary technique. An outside laboratory can perform the ancillary technique. "Pathologist" refers to any individual with training to evaluate laboratory specimens or the responsibility to evaluate specimens. Conventionally, a pathologist is a medical doctor that has completed a residency program accredited to train pathologist but in the present invention it could also mean a laboratory technician that conducts initial screen of pathology specimens. It could also mean the operator of a digital pathology platform that performs an initial screen of specimens. "Detection agent" refers to any chemical agent that is: visible at micro scale under standard light microscopy and physically stable in the presence of standard pathology stains.

The detection agent can comprise a paramagnetic bead of varying sizes. A 1 micron or 2.8 micron Dynabead® paramagnetic micropartice from Themofisher, for example, is reliably visible at micro scale and is compatible with standard stains. Similarly BioMag® superparamagnetic bead cluster, though less regular in shape, is still compatible with stains and visible in standard light microscopy. Solulink, Nanolink™ 0.8 micron magnetic bead clusters are similarly compatible and visible. Paramagnetic beads work due to the iron oxide's compatibility with standard stains and the beads' consistent, if not regular, size. Other materials that are compatible with standard stains, and visible during light microscopy could serve as a detection agent.

Referring now to FIG. 1, a 1 micron streptavidin-coated paramagnetic microparticle detection agent 1 is coupled to a biotinylated antibody to form a streptavidin-biotin linker system 2. In the present embodiment, the antibody is an antibody to CD 19 3. CD 19 is known B cell antigen and the present ancillary reagent construct forms a reagent that can identify B cells under normal anatomical pathology investigation.

For the embodiments disclosed in FIG. 1, the reagent performs a function similar to ancillary techniques—it identifies the presence of an antigen or possible antigens. Unlike other ancillary techniques, the reagent performs that function simultaneously during morphological investigation—in real time with standard light pathology. In this instance, the reagent makes it possible for the pathologist to differentiate B cells from T cells using standard light microscopy. Currently, both appear and stain as lymphocytes with no means to differentiate the two. The present ancillary reagent construct will appear proximal to B cells but not proximal to T cells. The pathologist will be able to identify B cells by the presence of the detection agent.

Figure 2:
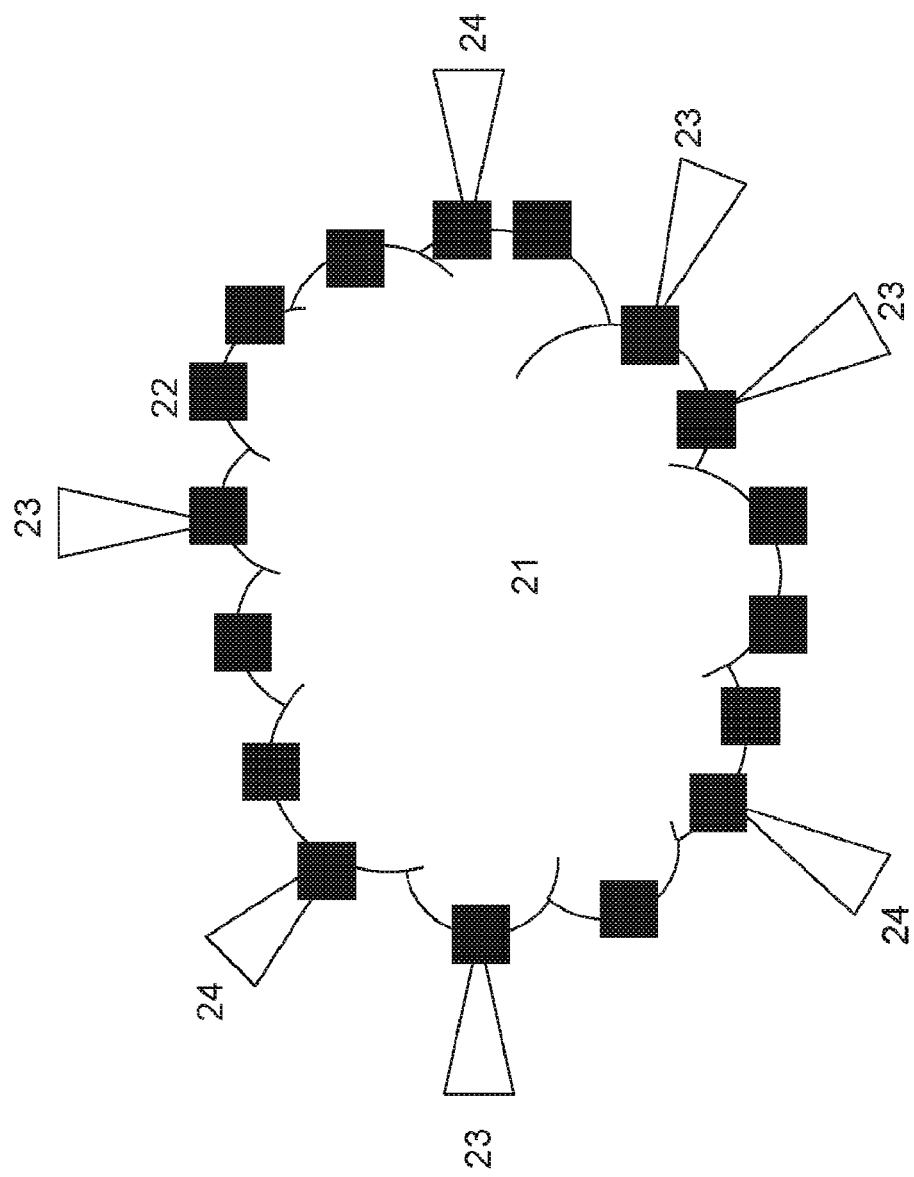
FIG. 2 is a diagram illustrating the structure, although not to scale, of a different embodiment of the ancillary reagent construct.

The ancillary reagent construct can comprise a variety of detection agents conjugated to a variety of antibodies. For example, referring now to FIG. 2, an alternative ancillary reagent construct comprises a Solulink, Nanolink™ 0.8 micron magnetic bead cluster as a detection agent 21 that is covalently coated with streptavidin 22. As with the prior embodiment, the antibodies are conjugates of Biotinylated rat anti-mouse Immunoglobulin G and IgG monoclonal antibodies to EpCam 23 and CEA 24. Both EpCam and CEA antigens are present on the surface of tumor cells found in body fluids.

In the present embodiment, it is important to note that the presence of the detection agent on a particular cell does not indicate the presence of a specific antigen, only the presence of one of multiple, possible antigens. Similar ancillary techniques focus on confirming the presence or absence of particular antigens. Flow cytometry, for example, utilizes antibodies conjugated to distinct flourochromes. The analysis provides quantification for each antigen on the surface of the cell.

The present embodiment only detects if one of a class of antigens is present. When coupled with morphological investigation under standard light microscopy, it makes possible simultaneous immunological and morphological investigation. For example, when investigating a body fluid specimen, a pathologist looks for cells that appear suspicious. Typically, they are epithelial cells that have the morphology of a tumor cell.

If a cell were to be borderline—some suspicious morphology but not definitive tumor morphology, then the pathologist must likely rely on ancillary techniques to get more information. The ancillary techniques run a panel of tests to determine if antigens like EpCam or CEA are present in the specimen. Ancillary techniques like flow cell blocks, immunoperoxidase or flow cytometry find antigens in the specimens. The findings do not correlate to specific cells that the pathologist can identify during anatomical pathology. The ancillary techniques inform the pathologist that the antigen is present in the specimen.

In the present embodiment, the ancillary reagent construct identifies specific cells, visible under standard stains that express either EpCam or CEA. The reagent identifies the cells by the proximal location of a detection agent to the cell that expresses the antigen. Any cell that expresses either EpCam or CEA that is present in a body fluid is highly suspicious. For suspicious cells with borderline morphology, the pathologist can integrate the presence or absence of a detection agent into the analysis. A single suspicious cell that has a detection agent proximal may need further ancillary analysis. Multiple suspicious cells that do not have detection agents proximal to them may require no further analysis.

The construct provides substantial immunological evidence to the pathologist while making a diagnosis based on cell morphology. The pathologist does not need to know the specific antigen, only that there is an antigen associated with the particular state or disease. The presence of the antigen and the cell morphology alone may not be enough to make a diagnosis. Together, they provide strong support for a clinical decision. A properly designed kit would allow a skilled pathologist to supplement morphological evaluation of samples with little specialized knowledge of relevant immunochemistry.

In the two aforementioned embodiments, detection agents comprise iron oxide microparticles or suspensions of magnetic microspheres. Both detection agents are selected for two essential properties: visibility under ordinary light microscopy and functionality under ordinary staining procedures. In the present embodiment, detection agents of approximately 1 to 2 microns produced outstanding results. The invention contemplates the use of larger or smaller detection agents as well.

Paramagnetic particles, generally, are used in the isolation and concentration of circulating cells in blood or other liquid matrices. The art has contemplated the use of paramagnetic particles as a detectable label that is conjugated to an antibody. The detection of the paramagnetic particle, however, is a function of the magnetic field that they generate. Instead of visualizing the presence of the particle like a detection agent, the art contemplates measuring the magnetic field produced by the particles. The use of paramagnetic particles is like other, more commonly utilized ancillary techniques. Paramagnetic particles, like radioactive of fluorescent conjugates, tell the pathologist that the antigen is present in the specimen. That analysis is wholly independent of the morphological analysis. The use of a label requires specialized equipment to identify a radiologic, fluorescent or magnetic signal.

In the present embodiments, the pathologist does not detect the presence of an antigen by measuring the magnetic field from the paramagnetic embodiments of the detection agent. The pathologist determines the presence of an antigen by visually confirming the detection agent proximal to the cell. Confirmation is done simultaneously with the morphological evaluation and it is done with standard light microscopy. Simultaneous analysis makes possible the integration of the ancillary analysis into the morphological investigation of a cell. For the first time ever, a pathologist can look at a cell's morphology and correlate it directly to the presence or absence of an antigen on the cell's surface.

Notwithstanding, other detection agents can be utilized to build different constructs. Glass microspheres, for example, could be used to make effective constructs. Similarly, microparticles made from other inert materials, such as polymers, metals or other elements could serve as effective detection agents.

Similarly, the streptavidin-biotin linker system is illustrative of the many ways to hybridize the immunoglobulins to the detection agent. The streptavidin-biotin system is preferable due to its ease of use and the covalent-like bond that it forms. Any other method of linking the immunoglobulin to the detection agent, such as avidin or neutravidin, could be used as well as other means of attaching the antibody to the detection agent.

Not all antibodies work with all detection agents. Particular combinations are the most effective. Table 1 shows which antibodies work with which detection agents.

| Detection Agent | 1 micron Dynabead ® | 0.8 micron Solulink Nanolink magnetic bead cluster | 2.8 micron Dynabead ® |
|---|---|---|---|
| Antibody | CD 3, CD 19 CD 20, LCA Lambda Light Chain, Kappa Light Chain CD 16, CD 68, CD 34 | HBME-1, EpCam CEA, CD34 | EpCam |

It is further contemplated in the present invention that factors related to antibody sensitivity, antigen density, membrane plasticity and the kinetic constraints of the detection agent influence the utility of ancillary reagent constructs.

Physical factors can constrain the ability of particular ancillary reagent construct to bind to a surface antigen. For example, in one embodiment, the linker is modified to include a spacer arm to the linker that further extends the antibody away from the detection agent. For example, Biotin-X-NHS from Calbiochem inserts a 6-atom spacer between the antibody and the detection agent. The spacer decreases the detection agent's hindrance of the antibody's ability to bind the target antigen. Similarly, other solutions that provide more space between the antibody and the detection agent would make it possible to have ancillary reagent constructs function with improved efficiency.

Figure 3:
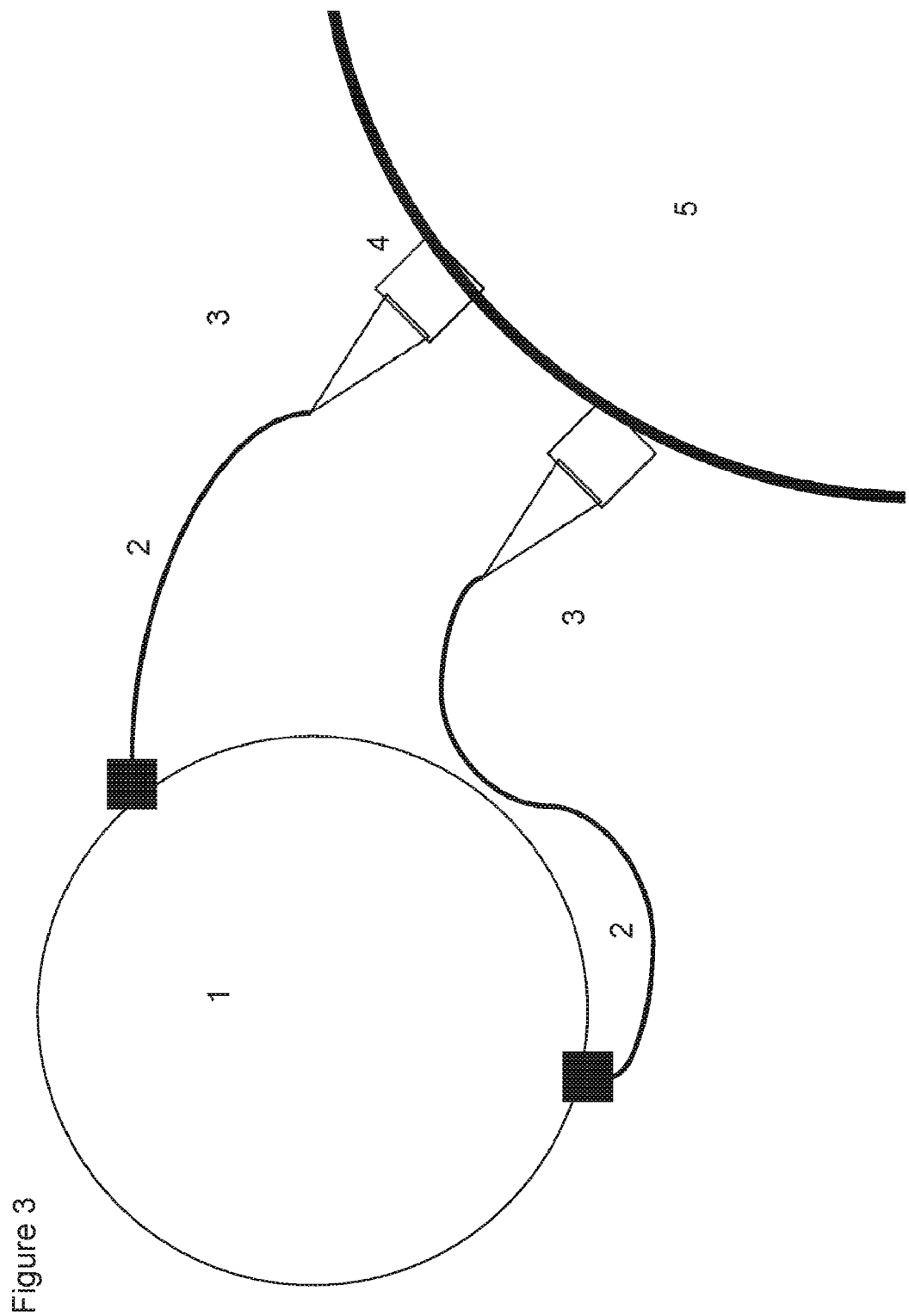
FIG. 3 is a diagram illustrating the structure, although not to scale, of an embodiment of the ancillary reagent construct with a modified linker to improve its binding efficiency.

FIG. 3 depicts an ancillary reagent construct with a modified linker 2 that improves the binding kinetics of the antibody's 3 binding of an antigen 4 on the surface of a cell. When compared to an ancillary reagent construct with a standard linker, such as the one depicted in FIG. 1, the present reagent is capable of binding antigens 4 that are more sparse on the surface of the cell or otherwise inefficient at binding the antibody 3 linked to the detection agent 1. For an ancillary reagent construct with a particularly large detection agent, like a 2.8 micron Dynabead® paramagnetic micropartice, the extended linker 2 can provide a boost in the efficiency in antigen 4 antibody 3 binding, which will ultimately make the detection agent 1 more visible, proximal to cells of interest to the pathologist.

The extended linker 2 need not be the Biotin-X-NHS product but can be any related means to compensate for antibodies 3 with limited binding capability, antigens 4 oriented on the cell surface 5 to present a challenge for antibody-antigen binding or very large detection agents 1 that constrain binding kinetics. In this manner, by making the linker more able to address the binding constraints of the selected antibody and the desired cell, the construction of the ancillary reagent can address a wide range of diseases or biological states. Even if an antibody has low binding capability or the target antigen is poorly disposed on the cell surface for immunostaining, several factors allow the engineering of constructs that would still be viable, alone or as part of a kits panel.

Modification of the linker is not the only way to enhance the binding capability of an ancillary reagent construct. The antibody or antibodies on the construct need not be selected to directly hybridize with a target antigen. For samples where the antigen density is so low that a monoclonal antibody to that antigen may not bind with sufficient efficiency to make for a functional construct, another approach is to use a primary antibody to attract the ancillary reagent construct to the cell.

In another embodiment, the present invention utilizes an ancillary reagent construct where the immunoglobulin is selected to hybridize not to the target antigen but to a primary antibody selected to bind to a target antigen.

Figure 4:
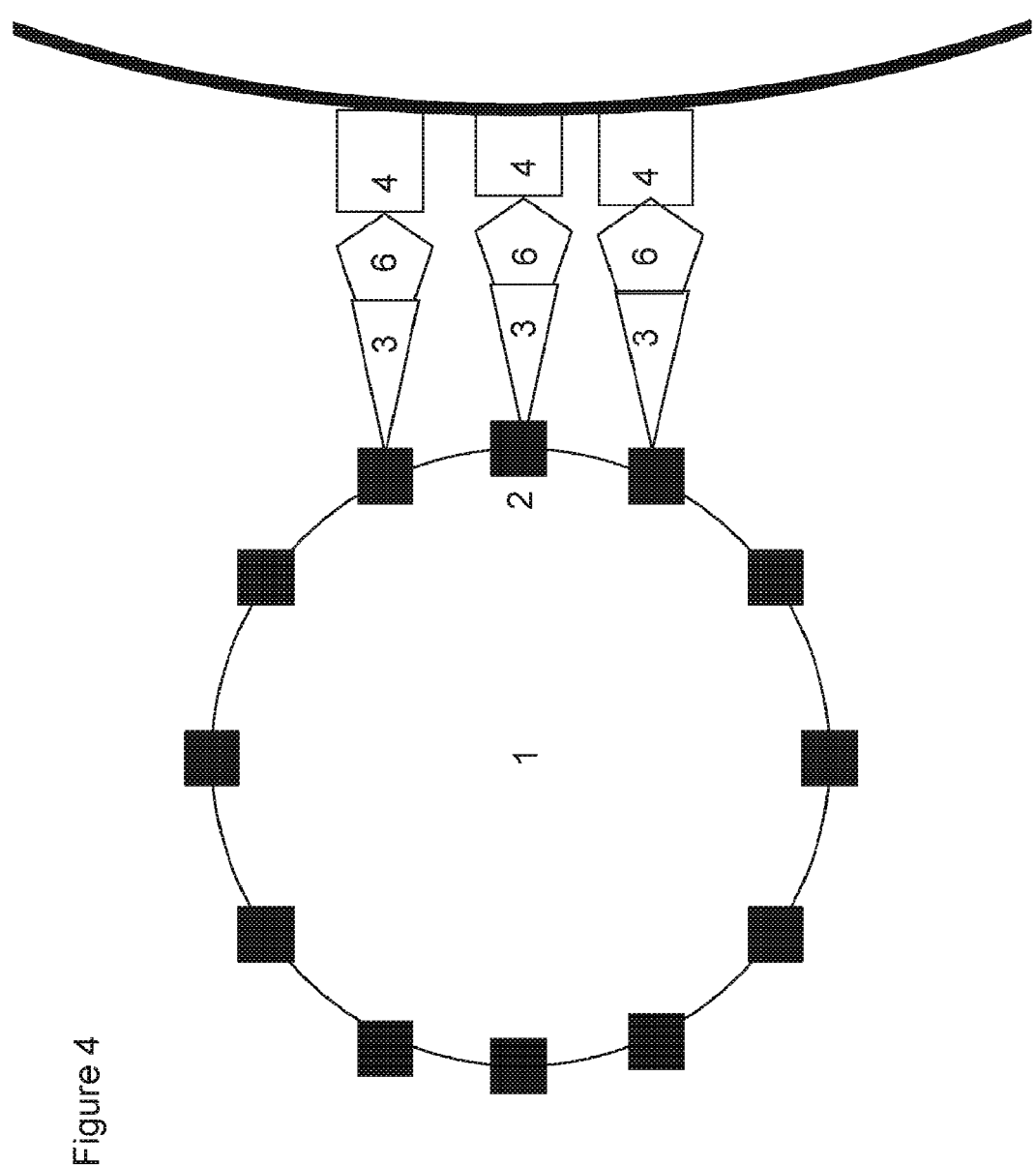
FIG. 4 is a diagram illustrating the structure, although not to scale, of the ancillary reagent construct utilizing a primary and secondary antibody to create indirect binding to a particular cell.

FIG. 4 depicts an aspect of the invention that is indirect, where a construct comprising a detection agent 1 that is attached to a primary antibody 3 through a linker 2. In all aspects, except for the selection of the antibody, the ancillary reagent construct is the same as practiced in the invention. For example, the reagent is conjugated to a goat anti mouse antibody. The antibody on the ancillary reagent construct serves as a secondary antibody selected to bind the primary antibody. Prior to administration of the ancillary reagent construct to the specimen, it is incubated with one or more secondary antibodies 6 selected to detect the presence of an antigen 4 on a cell 5.

The methodology is indirect because the construct never binds directly to the target antigen and instead binds to the primary antibody. The methodology makes possible the utilization of the construct on cells with antigens 4 that are, for whatever reason, unavailable to efficiently bind to an antibody. It also makes possible the utilization of antibodies 3 that are, for whatever reason, unable to efficiently bind to their target antigens to produce reliable results.

The ancillary reagent construct is like an ancillary technique for conventional pathology. It operates by placing a detection agent proximal to a cell that is positive for a relevant reagent, which is visible in the course of anatomical pathology conducted via light microscopy. Unlike all other ancillary techniques, the reagent can be administered during specimen processing for standard microscopy and allows for an ancillary analysis during light microscopy: simultaneous immunological and morphological investigation.

Various embodiments of the ancillary reagent construct accommodate antibodies with low affinity or specimens with sparse surface antigens. By varying the elements of the construct: the detection agent, the linker, and the antibody it is possible to produce a wide variety of reagents. Reagents can further be organized into panels and kits to facilitate the evaluation of specific diseases and biological states.

Method for Simultaneous Immunological and Morphological Investigation

Disclosed herein are embodiments that comprise a series of steps for simultaneous immunological and morphological investigation. During a pathologists examination of specimen, when morphology is insufficient to confidently recognize an abnormal cell, the pathologist can use the presence or absence of the detection agent to facilitate diagnosis.

Figure 5:
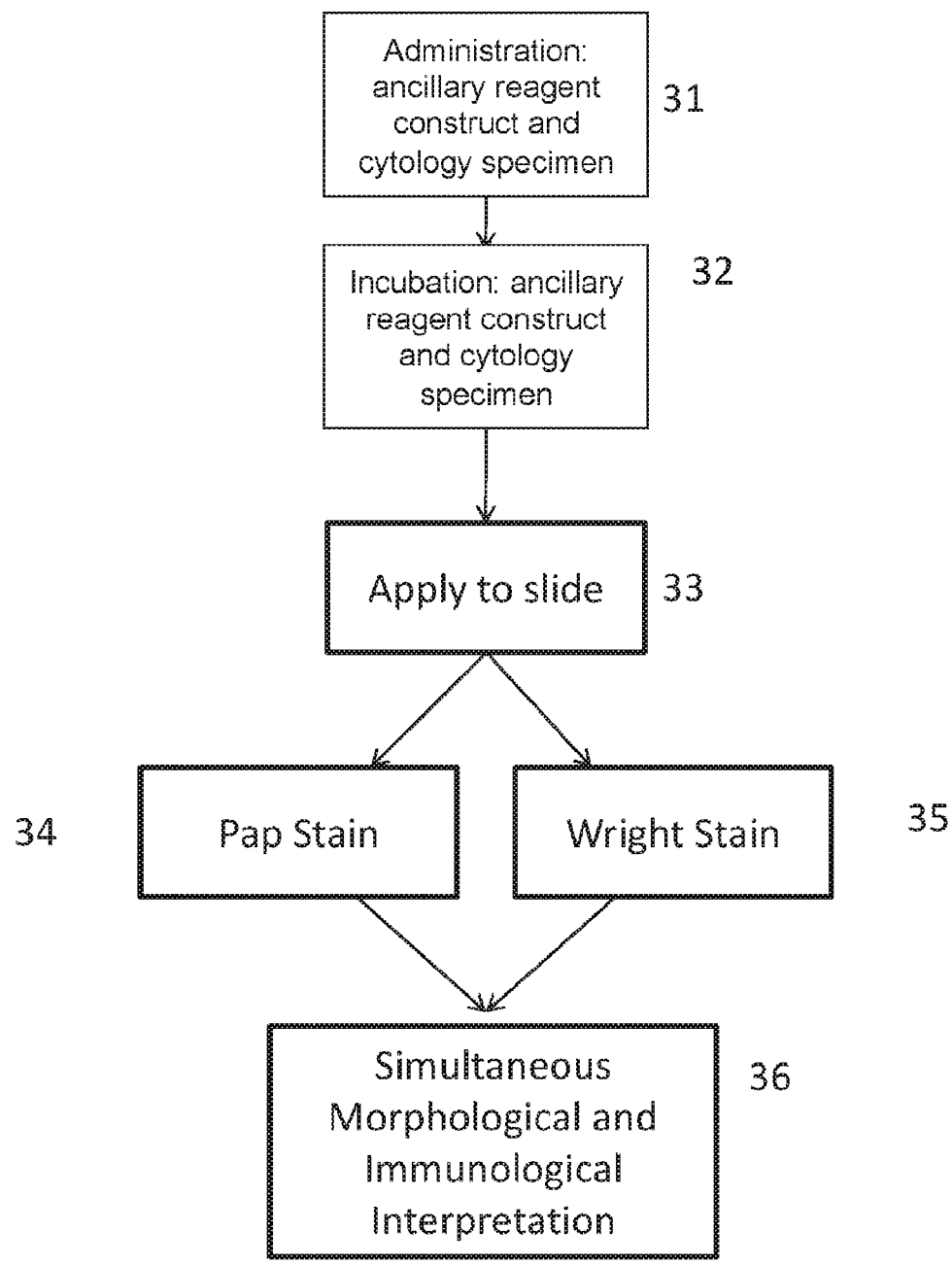
FIGS. 5 and 6 are flow charts illustrating the process of simultaneous immunological and morphological analysis.

Referring now to FIG. 5, the diagram depicts the integrated workflow for utilizing the reagent in standard cytopathology. Evaluation begins at 31 where the construct and a cytology specimen are incubated so as to facilitate attachment of the antibodies to antigens on the cells.

Generally, incubation must approximate liquid phase kinetics; the specimen is a suspension of cells and, in the envisioned embodiments, the constructs are administered suspended in liquid. It is important to know the general concentration of the reagent and the concentration of the cells of interest to insure the correct proportions. To that end, the specimen should undergo some form of cell counting, which can be a conventional laboratory cell count or whole slide imaging applications.

In order to obtain more readable results, the ancillary reagent construct must be appropriately proportioned to the number of cells in the specimen. A slight excess of reagent to cells ensures that there is adequate reagent to bind available antigen but minimizes non-specific cross-reaction between ancillary reagent constructs. Too little reagent produces no meaningful results. Too much produces aggregates of self-binding reagent. The correct ratio differs based on the specimen under evaluation and the antigens targeted by the reagents. For example, whole blood samples determined to exhibit absolute lymphocytosis require 1:40 dilutions and need to be incubated with 1:50 dilutions of ancillary reagent construct.

The concentration of the ancillary reagent construct is a function of the detection agent. For 1 micron Dynabead® paramagnetic microparticles, the concentration for a 1/50 dilution of a stock solution is approximately 20,000 microparticles/microliter. The ratio is approximately 20 beads/leukocyte in blood, for example and 40 beads/cell in body fluids. Ancillary reagent constructs that use different sized detection agents have different concentrations. For example, the corresponding number of 2.8 micron Dynabead® paramagnetic microparticles is about 10 times less. The present concentrations are given purely as examples. Different detection agents produced from different materials could produce wildly different concentration. Nothing in the present discussion of concentrations is intended to limit the scope of potential useful concentrations for practice of the invention.

Other kinds of specimens have differing concentrations of cells. An effective cellular concentration for peripheral blood and bone marrow specimens is around 1000 cells/microliter. For lymph node biopsies and body fluids the concentration is around 500 cells/microliter. Cell concentration for urines and other kinds of fine needle biopsies can be even more variable. It is always possible to count the cells utilizing standard laboratory methodologies in order to quantify the correct amount of ancillary reagent construct to administer. Specimens produced from human bodies will have to vary in the concentration of cells. Nothing in the present discussion of concentrations is intended to limit the scope of potential useful concentrations for practice of the invention.

FIG. 5 depicts one exemplary protocol. Body fluids 5, once administered, the body fluid and the construct are 32 agitated for 30 minutes at room temperature. Agitation facilitates exposure of the ancillary reagent construct to the cells and better approximates the liquid phase kinetics. A variety of means of agitation such as orbital shaking, tilt shaking or other standard laboratory methods are sufficient to prepare the sample. Moreover, depending on the kinetics of the immunoglobulin hybridization with antigen, gentler or more aggressive agitation, at different temperatures, may facilitate the present method.

After agitation, the method of preparation closely follows standard clinical cytopathology methods. The sample is placed on a cytospin slide 33 and spun to form a smear. The sample is then stained with a standard cytological stain 34, 35 and undergoes simultaneous immunological and anatomical examination under light microscopy 36.

Based upon the body fluid and the suspected malady, the pathologist can select from a wide range of constructs to incubate and agitate with the specimen 32. The compatibility of the constructs with standard stains provides wide flexibility in determining a diagnostic strategy. For example, the use of an ancillary reagent construct that comprises antibodies against antigens associated with reactive cells present in pleural fluids allows a pathologist to rule out neoplasm in morphologically suspicious cells. Such a reagent could be an ancillary reagent construct. The presence of the detection agent near a morphologically suspicious cell would strongly support that it is a reactive cell.

Figure 6:
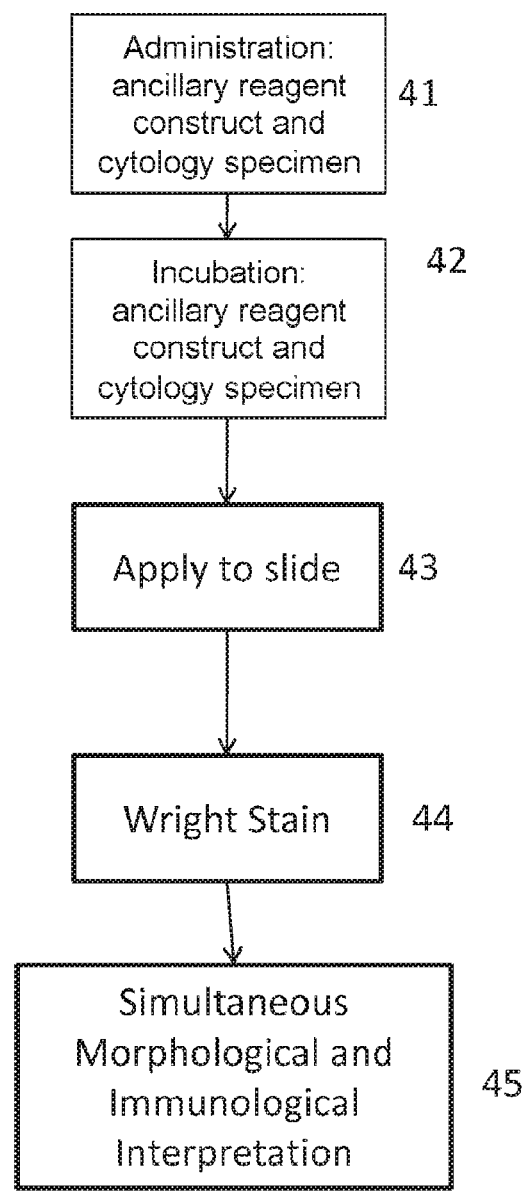

Looking now to FIG. 6, the process for preparing a specimen contains a small number of critical deviations in the preparation of a body fluid 41. The specimen and the ancillary reagent construct are then agitated 42 and spun down onto a slide 43. The specimen is stained with a wright stain 44 and then undergoes simultaneous morphological and immunological interpretation 45.

Additional steps can dramatically enhance the present method. For example, access to cell surface antigens can be inhibited by the presence of an extracellular matrix. The extracellular matrix can cover the antigens and serve as a barrier that prevents the binding of antibodies. The present method can further incorporate enhancements to overcome this and other problems.

Deviations in the protocol are not limited to the preparation of specimens. Changing light microscopy conditions can change the utility of the reagent. For example, increasing the contrast in the image helps to visually indicate when the ancillary reagent constructs are present near a target cell. By removing the birefringence filter from the microscope changes the contrast and makes the detection agents more discernable and visible. It is possible to identify the cells of interest with filter in place and then remove the birefringence filter in order to better identify or quantify the visible detection agents from the ancillary reagent construct.

Additionally, the present invention can also facilitate digital pathology. Currently, many digital pathology approaches rely upon the application of image recognition technology to distinguish normal as opposed to abnormal pathology. The challenges for such digital pathology approaches are similar to the challenges facing the typical pathologist. Simultaneous Immunological and Morphological Investigation, through the methods and constructs taught in this invention, show potential to be even more useful in the field of digital pathology. A computer that utilizes image recognition to identify morphological features associated with disease. Simultaneous Immunological and Morphological Investigation introduces a binary decision about the presence or absence of one or more antigens. Utilizing Simultaneous Immunological and Morphological Investigation will make digital image recognition digital pathology much simpler.

Ancillary Kits

Disclosed herein are embodiments that comprise reagents and methods that make possible simultaneous immunological and morphological investigation of pathology specimens. For example, in some embodiments, a kit contains one or more reagents organized into panels. Each reagent is a detection agent conjugated to one or more antibodies. The antibodies are selected to bind antigens associated with a disease or biological state of interest. The ancillary reagent construct is administered to pathology specimens and visualized in the course of ordinary anatomical pathology: making possible simultaneous immunological and anatomical investigation.

A single kit comprises a reagent panel or panels of reagents that identify relevant antigens. The organization of the kit facilitates the stepwise application of reagent panels to make clinically relevant decisions. The selection of the reagents in the panels and which panels are included in the kit create ancillary kits focused for particular application. The application of each panel adds information that enhances morphological evaluation and helps the pathologist make decisions based on cell morphology.

Various examples of ancillary kits are disclosed below. The inclusion or absence of particular kits is not limiting as to the scope of the invention, neither is the selection of particular reagents or reagents with particular antibodies. The kits operate not by making a definitive diagnosis based on the presence or absence of a reagent but instead integrates the absence or presence of an antigen into the morphological interpretation. The ancillary reagent construct and associated methods for producing simultaneous immunological and morphological investigation make possible a multiplicity of ancillary kits for a variety of applications.

In all applications, the kit involves incubating a sample in the presence of an ancillary reagent construct and then preparing a slide for standard light microscopy. The present kits focus on the selection of reagents and the order of panels. The practice of the method, as previously described, is not recited in the description of the present kits. Notwithstanding, the preparation and analysis of slides—anatomical pathology—is a presumed practice associated with all the present kits. Moreover, when panels comprise multiple ancillary reagent constructs, each panel will require evaluation on a separate slide. Oftentimes, the pathologists evaluation will consider the results of multiple slides.

It is further contemplated that a kit would include a positive and negative control. Such controls could be similar to the controls used in flow cytometry. Cells grown to have standard antigen density or cell-sized beads that are coated with standard concentrations of antigens would be valuable to run along with panels. The control would have an expected density of detection agents proximal to them. Such a control would give the pathologist confidence in negative results: when suspicious cells do not have any detection agents proximal to them.

Each kit is more than a particular selection of antibodies, but a prescription of antibodies to follow up a particular anatomical observation. The kit allows a pathologist with anatomical experience to leverage information about cell surface antigens, simultaneously, in order to enhance confidence in the diagnosis.

Example 1: Hematology/Pathology Kit

A complete blood count (CBC) is one of the most fundamental lab tests performed in clinical laboratories. One element of the CBC is a lymphocyte count. An elevated lymphocyte count can be the result of an infection but it can also be cancer. Currently, the only way to determine if lymphocytosis is possible infection (reactive) or cancer (neoplastic) is an ancillary technique like flow cytometry.

For example, chronic lymphocytic leukemia (CLL) is a disorder especially present in the elderly. In its early stage, CLL presents as an elevated lymphocyte count and is difficult to distinguish from the more common reactive lymphocytosis. Distinguishing CLL from reactive lymphocytosis requires a determination of the clonality of the surface antigens of the component lymphocytes. Current methods utilize flow cytometry, which result in expense and delay. Rather than test for clonality upon recognition of absolute lymphocytosis, the pathologist will follow up later to see if the lymphocytosis has resolved.

Figure 7:
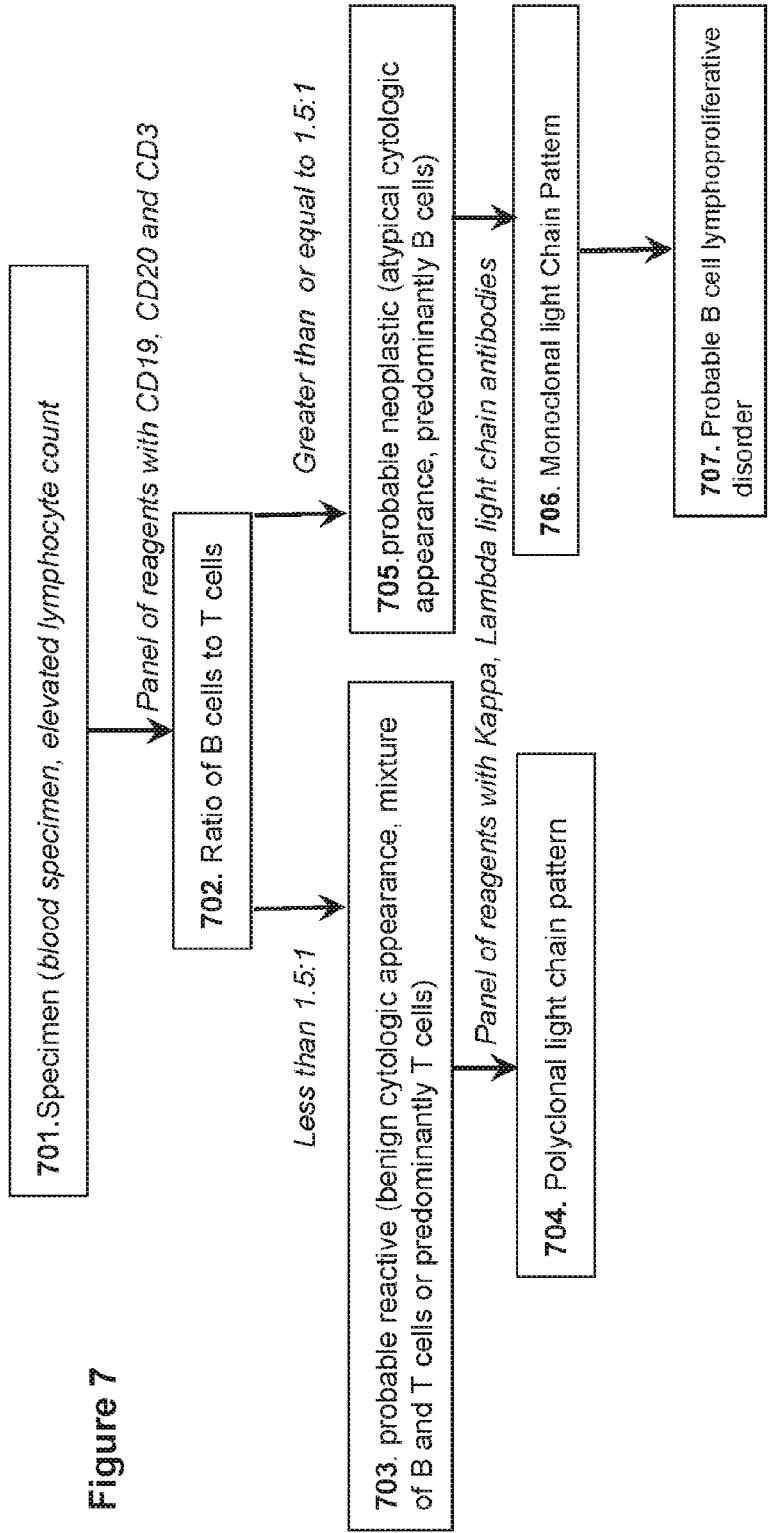
FIG. 7 is a flow chart illustrating the application of a hematology/pathology ancillary kit to specimens exhibiting lymphocytosis.

In one embodiment, the present invention is a kit for identifying neoplastic B cells; it is of particular use in differentiating reactive from neoplastic lymphocytosis. Looking now to FIG. 7, the kit begins with a blood specimen identified as having an elevated lymphocyte count 701. The kit uses two panels of ancillary reagent constructs. The first panel includes reagents with antibodies to B cell antigens: CD 19, CD 20 and reagents with an antibody to CD 3, a T cell reagent.

In the present kit, each reagent would produce a different slide. At the end of the first panel, in some embodiments, the pathologist will have 3 slides to review. The pathologist can then take the total ratio of B cells to T cells 702. The panel would be able to differentiate B cells from T cells. If the ratio exceeds 1.5:1 B cells to T cells then the specimen may be undergoing neoplastic lymphocytosis.

FIG. 7A is a photomicrograph of a specimen evaluated using the first panel. The specimen is a blood smear, which, in this slide has undergone evaluation with an ancillary reagent construct that is conjugated to an antibody to CD 20. The detection agent is a 1 micron Dynabead® paramagnetic microparticle. The specimen is then stained with a wright stain under standard protocols.

In FIG. 7A, the lymphocytes 710 (stained purple) that have detection agents 711 localized on their surface have CD 20, a B cell antigen, expressed on their surface. Apart from the presence of the detection agent, they are morphologically identical to T cells (not pictured).

Figure 7B:
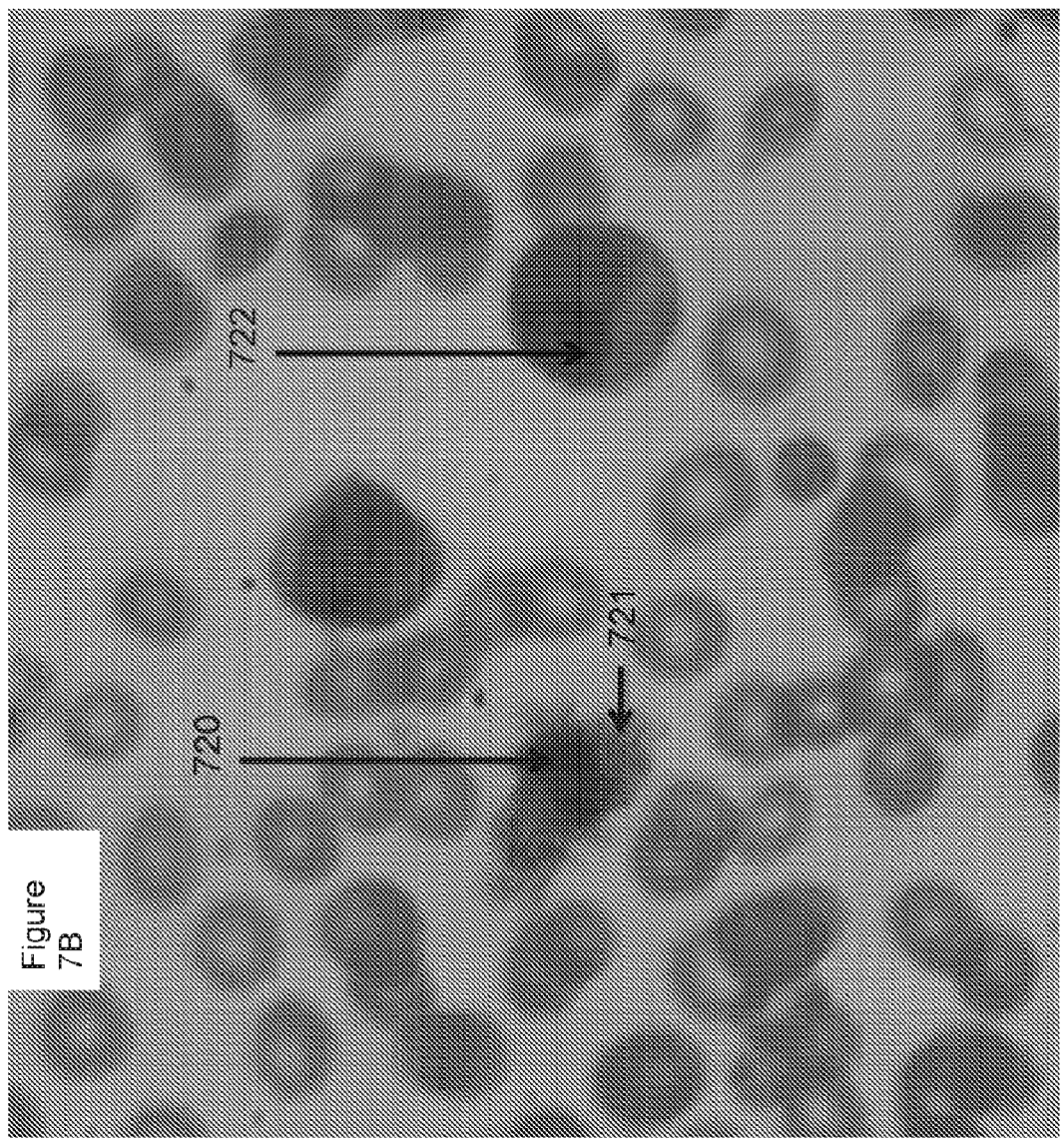

Similarly, FIG. 7B is a photomicrograph of a specimen evaluated using the first panel. The specimen is a blood smear, which, in this slide has undergone evaluation with an ancillary reagent construct that is conjugated to an antibody to CD 20. The detection agent is BioMag® superparamagnetic bead cluster. The specimen is then stained with a wright stain under standard protocols. In 7B, nearly all of the lymphocytes in the specimen did not exhibit the detection agent 721. That observation strongly supports that the specimen is an instance of reactive lymphocytosis because of the lower ratio of B 720 to T 722 cells.

As in FIG. 7B, if the ratio of B cells to T cells is less than 1.5:1 then the specimen is likely reactive 703. Continued analysis utilizing the next panel in the kit would further establish the specimen as reactive. Incubation the specimen with a panel of reagents that includes Kappa and Lambda light chains, if the specimen is reactive, would produce a polyclonal light chain pattern 704. To evaluate the light chain pattern, the pathologist will compare the ratio of lymphocytes positive for kappa light chain and positive for lambda light chain. For example, elevated kappa or lambda can indicate monoclonality: a 3:1 kappa to lambda ratio or a 2:1 lambda to kappa ratio strongly indicates monoclonality.

It is important to note, in the evaluation of the slides produced using the kit, that the pathologist must examine both the morphology and the presence or absence of the reagent. For example, in the blood smears in FIGS. 7A and 7B, the pathologist can identify which cells are lymphocytes based on their morphology. The reagent gives more information: if B cell or T cell antigens are present. In order to establish the ratio of B cells to T cells the pathologist will need the reagent in conjunction with the morphological evaluation of the specimen. In that way, the additional information made possible from the ancillary kit transforms the light microscope by adding information about the immunological state of the cell, which can be simultaneously considered with the cell's morphology.

Figure 7C:
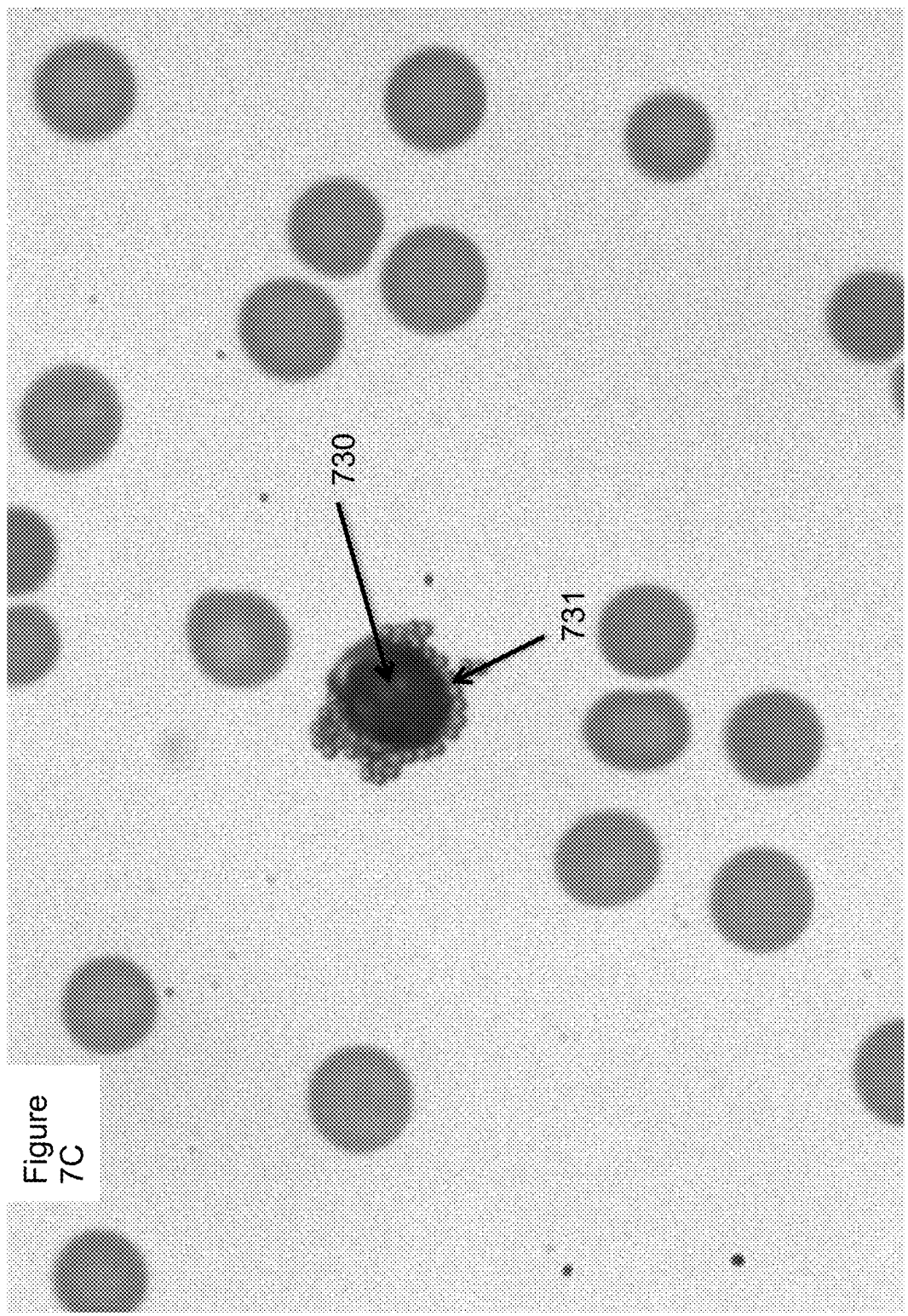

FIG. 7C is a photomicrograph of a specimen evaluated using the first panel. The specimen is a blood smear, which, in this slide has undergone evaluation with an ancillary reagent construct that is conjugated to an antibody to CD 3. The detection agent is a 1.0 micron Dynabead® paramagnetic microparticle. The specimen is then stained with a wright stain under standard protocols. CD 3 is a T cell marker and the presence of the detection agent 731 near the lymphocyte 730 strongly indicates that the lymphocyte is a T cell.

For samples where the ratio 705 of B cells to T cells is greater than 1.5:1 the pathologist further examines the specimen with reagents with antibodies to kappa and lambda light chains. Utilizing the first panel, a pathologist can identify the ratio of T cells to B cells both by direct examination as well as indirect examination. For slides from specimens incubated with a reagent designed to detect B cells (such as FIGS. 7A and 7B), the pathologist can determine the ratio of B cells to T cells by looking at cells with detection agents present (B cells) and cells with detection agents absent (T cells). The pathologist can then verify that results by looking at the reagents that detect T cells. Both slides are from the same specimen and both give information about its biological state. Taken together, they allow the pathologist to make a confident projection of the B cell to T cell ratio.

The pathologist then applies the second panel, which establishes if B cells are monoclonal. What differentiates reactive from neoplastic lymphocytosis is the presence of monoclonal B cells. The first panel establishes if the B cell ratio is elevated in a specimen. The second panel uses ancillary construct reagents that are conjugated to antibodies against Kappa and Lambda light chains. The pathologist compares slides incubated with a reagent conjugated to an antibody against kappa light chain to slides incubated with a reagent conjugated to an antibody against lambda light chain and determine the ratio of lambda to kappa light chains 706. A 3:1 kappa to lambda ratio or a 2:1 lambda to kappa ratio indicates that the B cell is monotypic, which strongly indicates the specimen is neoplastic.

Figure 7D:
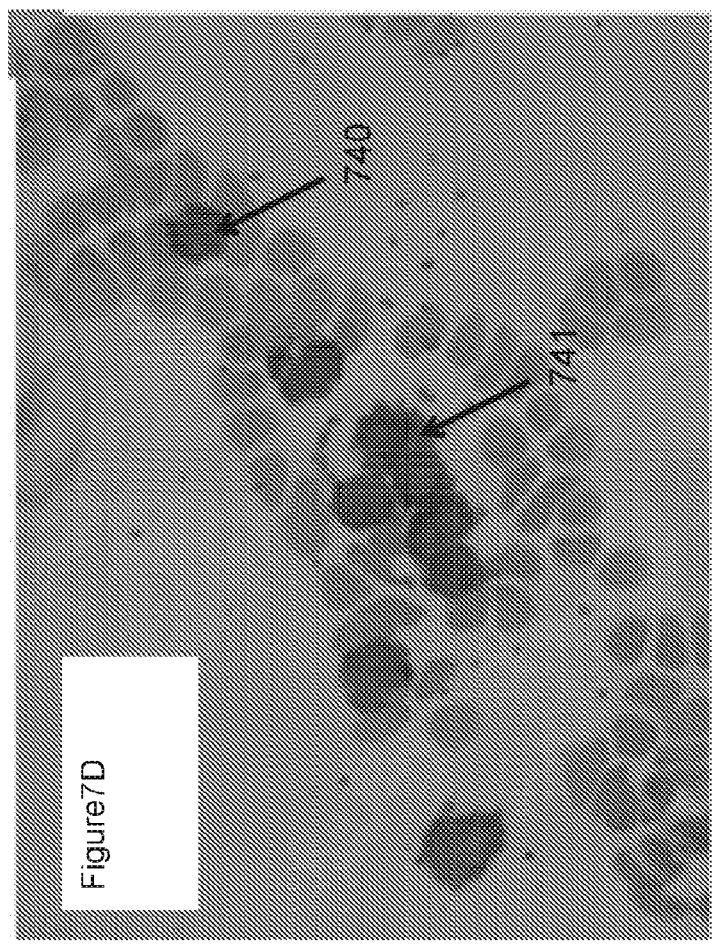

FIG. 7D is a photomicrograph of a specimen evaluated using the second panel. The specimen is a blood smear, which, in this slide has undergone evaluation with an ancillary reagent construct that is conjugated to an antibody to lambda light chains. The detection agent is a 1.0 micron Dynabead® paramagnetic microparticle. The specimen is then stained with a wright stain under standard protocols. As part of a panel that includes reagents conjugated to antibodies to kappa light chain, the panel provides guidance to establish if the specimen is reactive or neoplastic.

In FIG. 7D, the majority of lymphocytes 740 also have detection agents 741 present proximal to their cell surface. The presence of the detection agent indicates that they are positive for lambda light chains. Specimens incubated with ancillary reagent constructs conjugated to anti kappa light chain antibodies saw no proximal localization of the detection agent. That result strongly supports that the B cells, as identified in the previous panel, are producing the same kind of antibody. They are monoclonal and monoclonality is a strong indicator that the lymphocytosis is due to neoplasm 707.

Figure 7E:
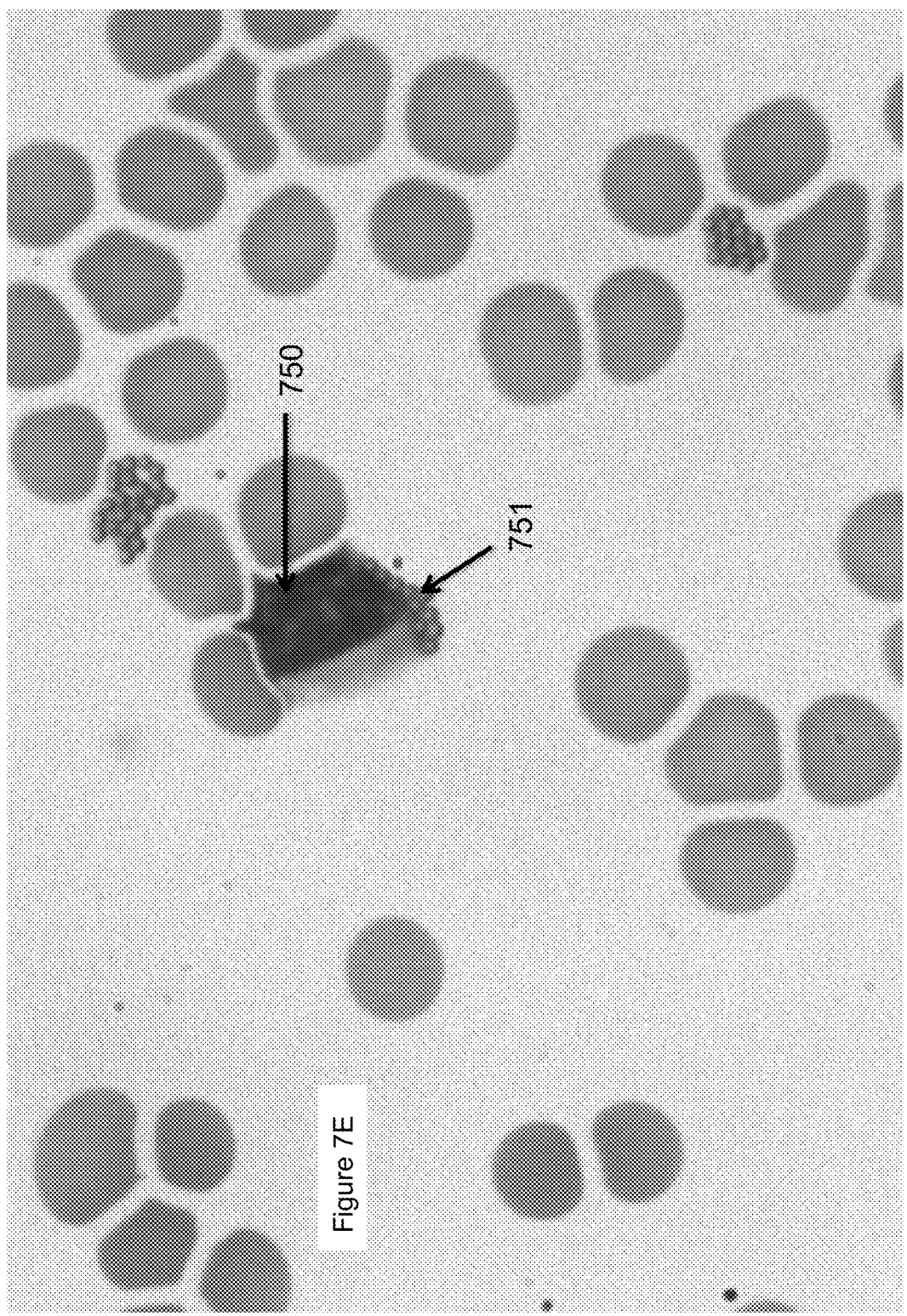

FIG. 7E is another photomicrograph of a specimen evaluated using the second panel. The specimen is a blood smear, which, in this slide has undergone evaluation with an ancillary reagent construct that is conjugated to an antibody to kappa light chains. The detection agent is a 1.0 micron Dynabead® paramagnetic microparticle. The specimen is then stained with a wright stain under standard protocols.

The composition of reagents in the panels in the kits is, by no means, limited to the embodiments described above. Other kits could include different first panels with reagents to antibodies to other pan B cell antigens: CD24, CD72 and CD73. Different kinds of reagents could also facilitate different kinds of analyses. For example, a panel of reagents with antibodies to T cell antigens, like T4 and T8, would require evaluation of the ratio of T4 to T8 positive cells. Most cell neoplasms are T4 positive and T8 negative, which makes the nature of the evaluation a bit different.

The panels could also be replaced with reagents that are conjugated to multiple antibodies. For example, a B cell panel comprising CD 19 and CD 20 could be replaced with a single reagent conjugated to both CD 19 and CD 20. The pathologist would not know if the particular lymphocyte is positive for a specific reagent but the reagent would establish if a lymphocyte is a B cell or a T cell.

Other than differentiating neoplastic vs. reactive instances of absolute lymphocytosis, the present kit has other applications. For example, a fine needle biopsy of a lymph node would potentially contain lymphoctyes that need to be identified and established as neoplastic or reactive. Similarly, body fluids can contain B cells, which should be investigated to determine if they are neoplastic or reactive. For example, a pleural effusion can be the presentation of a primary lymphoma, which would require investigation of free B cells in the specimen. In either case, the ratio of T to B cells would be less relevant to facilitate the morphologic diagnosis. Identifying a lymphocyte in the specimen would warrant further investigation as to if it is monotypic or not.

In that aspect of the present invention, kits are presented to investigate the anatomy and state of particular kinds of cells that may be present in specimens. The kit is a collection of reagents and protocols that provide additional information to the current practice of anatomical cytopathology. The protocol, with de minimis deviation can be applied to a wide variety of instances and help the pathologist make an anatomical diagnosis.

Example 2 Body Fluid Kit

In the evaluation of any body fluid specimen, such as an abdominal fluid, pericardial fluid or pleural fluid, the pathologist's primary goal is not to miss a positive diagnosis. In current practice, the pathologist evaluates a slide morphologically to find any cells that are morphologically suspect. The pathologist must evaluate every cell in the specimen to rule out suspicious morphology.

The slide may contain a population of cells that are anatomically definitive and the pathologist can diagnose the body fluid as malignant. The slide may also contain a population of cells that are anatomically borderline. In that case, the pathologist will likely send the specimen for evaluation by ancillary techniques, such as a cell block or immunoperoxidase.

Figure 8:
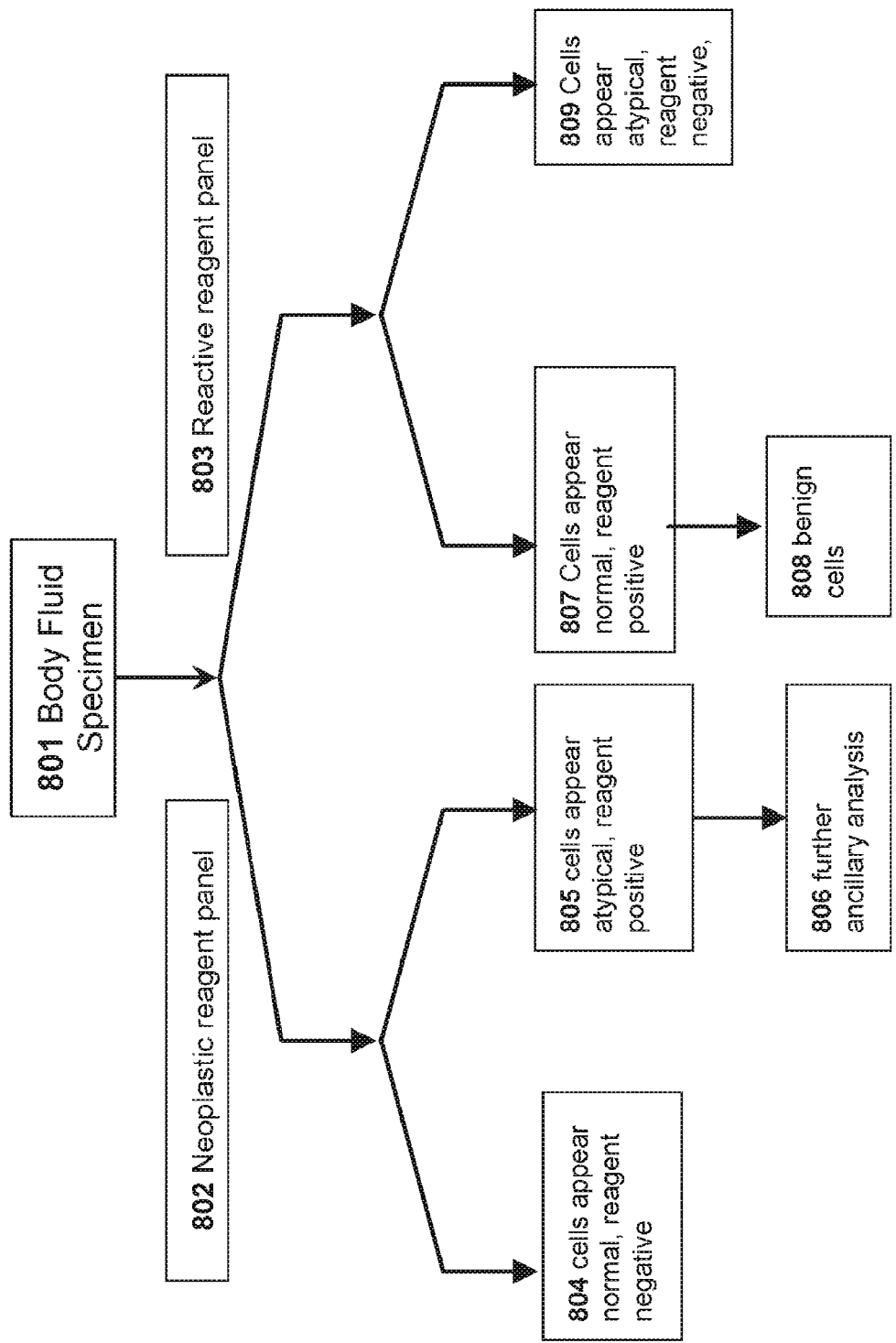
FIG. 8 is a flow chart illustrating the application of a body fluid ancillary kit to body fluid specimens.

In one embodiment, the invention is a kit that augments a pathologist's anatomical investigation of a body fluid. The kit comprises two distinct panels of ancillary reagent constructs. One panel is sensitive to antigens expressed on reactive cells and the other is sensitive to antigens expressed on neoplastic epithelial cells. Looking now to FIG. 8, analysis begins with a body fluid sample 801. In most instances, the body fluid will be abdominal fluid, pericardial fluid or pleural fluid. Without limiting the scope of possible body fluid samples, the present kit could also be used with a wide variety of other, less common fluids. Fluid from pancreatic lesions, for example, is a less common body fluid that undergoes similar analysis.

The kit comprises two panels: a neoplastic panel and a reactive panel. The neoplastic panel 802 comprises at least two ancillary reagent constructs: one conjugated to an antibody to EPCAM and another to an antibody against CEA. EPCAM is an antigen that serves as an adhesion molecule and is present in almost all carcinomas and malignancies. EpCam's high concentration makes it a good target for the reagent. Some tumors, however, are EPCAM negative. Lobular breast cancer for example, does not express EPCAM on its surface but does express CEA. Together, EPCAM and CEP comprise the neoplastic panel that will help a pathologist identify most tumors.

In one embodiment, the first panel comprises an anti-EPCAM antibody are conjugated to a 2.8 micron paramagnetic microparticle and CEA conjugated to a Solulink, Nanolink™ 0.8 micron magnetic bead cluster. Notwithstanding, reagents conjugated to antibodies to other reagents are also worth considering. For example, other antigens associated with tumor cells present in body fluids, CD15, Berep4, ecad, and EMA, could be included in or replace existing members of the panel.

The reagents in the kit supplement standard anatomical cytopathology. For example, if the pathologist examines slides treated with the neoplastic panel, the cells appear normal and there are no detection agents present that are proximal to the normal-appearing cells then the pathologist can be more confident that the cells are not neoplastic 804. Alternatively, if the cells have characteristics of neoplastic cells, such as a high nuclear/cytoplasmic ratio, or are otherwise atypical then the presence of the detection agent, proximal to the cell surface, 805 provides supplemental information that antigens associated with neoplastic cells are on the surface. In such instances, further analysis by ancillary techniques 806, like cell blocks or immunoperoxidase, may be warranted.

Figure 8A:
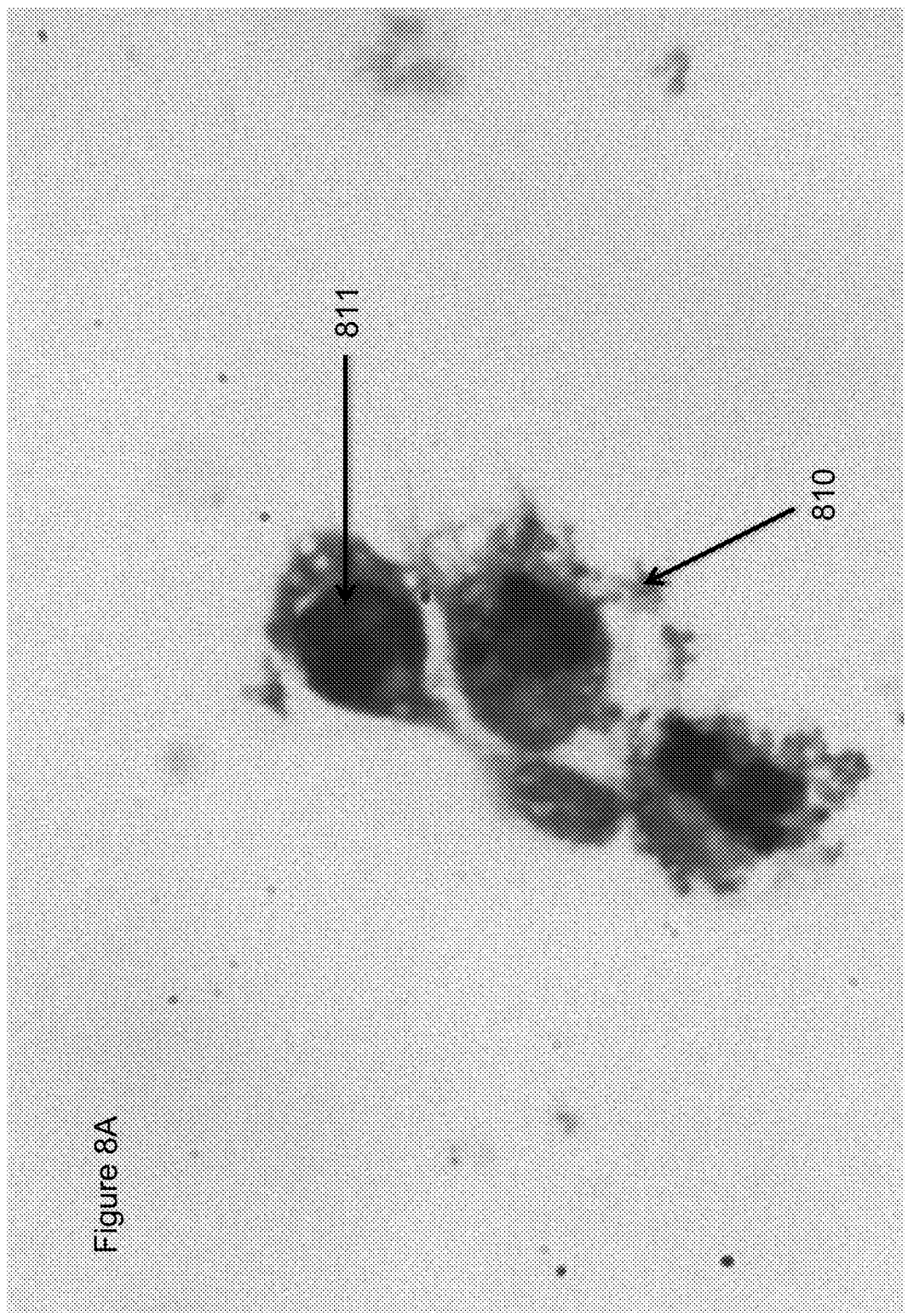

FIG. 8A is a photomicrograph of a specimen evaluated using the neoplastic panel. The specimen is a pleural fluid, which, in this slide has undergone evaluation with an ancillary reagent construct that is conjugated to an antibody to CEA. The detection agent is a Solulink, Nanolink™ 0.8 micron magnetic bead cluster. The specimen is then stained with a wright stain under standard protocols. The detection agents 810, which are proximal to the tumor cells 811, strongly support that the cells are neoplastic.

In the photomicrograph, the cells 811 appear atypical. The presence of the detection agent 810 on the surface of the cell strongly supports that it is neoplastic. The specimen will likely undergo further analysis using an ancillary technique, such as a cell block or immunoperoxidase.

FIG. 8B is a photomicrograph of a specimen evaluated using the neoplastic panel. The specimen is a pleural fluid, which, in this slide has undergone evaluation with an ancillary reagent construct that is conjugated to an antibody to EpCam. The detection agent is a 2.8 micron Dynabead® paramagnetic microparticle. The specimen was stained with a standard wright stain, rendering the cells 820 visible. The detection agents 821, which are proximal to the tumor cells, strongly support that the cells are neoplastic.

Figure 8C:
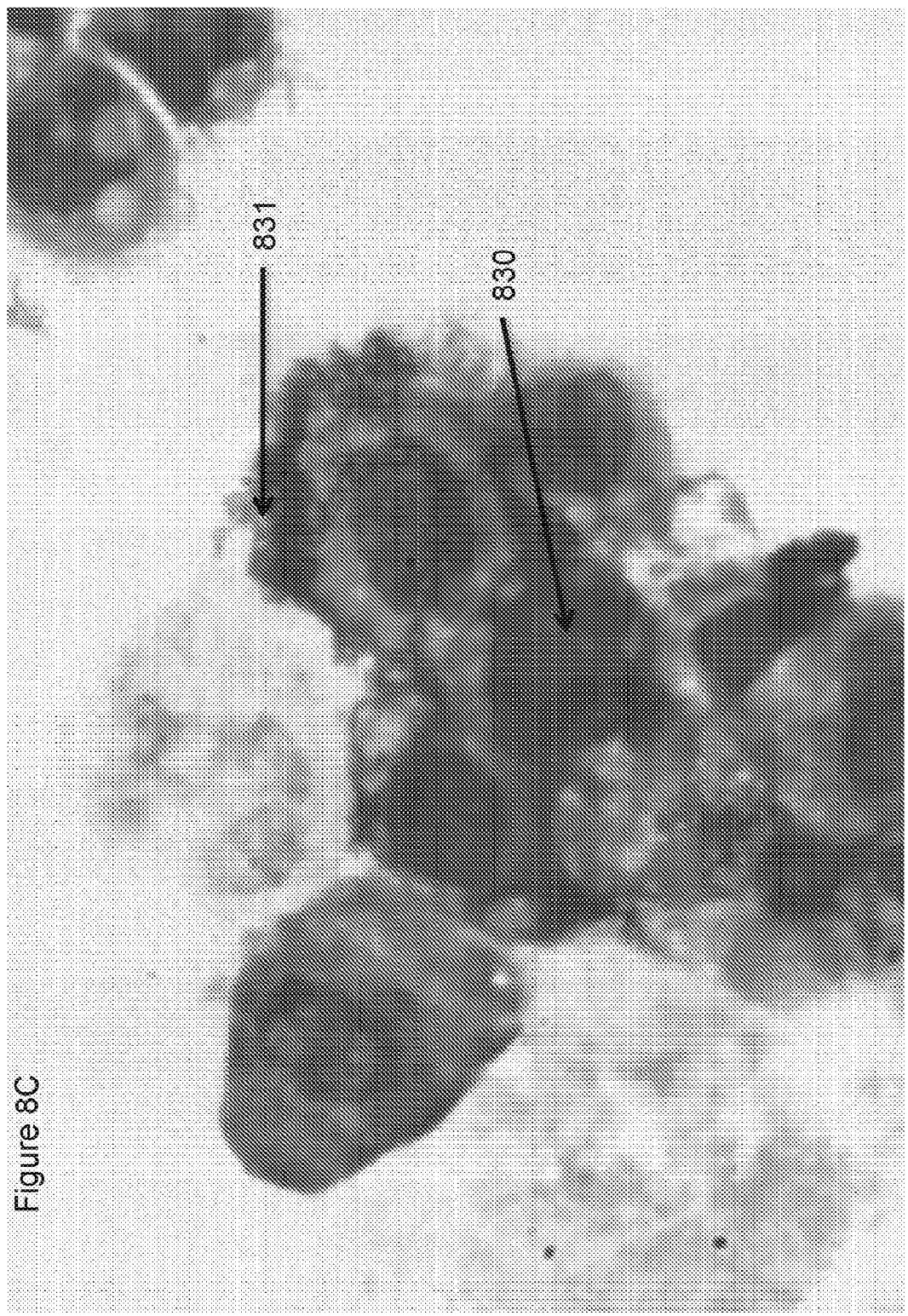

FIG. 8C is a photomicrograph of a pleural fluid specimen evaluated using the neoplastic panel. The specimen is a pleural fluid, which, in this slide has undergone evaluation with an ancillary reagent construct that is conjugated to antibodies to both EpCam and CEA. The detection agent is a Solulink, Nanolink™ 0.8 micron magnetic bead cluster. The specimen is then stained with a wright stain under standard protocols.

Unlike FIG. 8A or 8B, the presence of the detection agent 831 on the surface of the cell 830 does not identify a particular antigen on the surface of the cell. It means that either EpCam or CEA are expressed on the cell surface. In either case, the cell is neoplastic, which is the relevant fact. In that aspect, the entire neoplastic panel 802 is present in a single reagent.

In manufacturing the reagent, a mixture of 50 microliters of EpCam antibody and 20 microliters of CEA antibody is used (commercial concentrates). The rationale is that almost all carcinomas are positive for EpCam. The reagent disproportionately needs to identify when EpCam is present on the surface of a cell. CEA, however, is an antigen present on lobular breast carcinoma. Not even the most common breast carcinoma, its inclusion is to cover the kinds of tumor cells that would not otherwise be positive for EpCam.

The present kits and their constituent panels and reagents, as embodied in the present invention, can similarly be practiced as multi-antibody reagents such as shown in FIG. 8C. So long as the antibodies all indicate the same relevant biological state. In 8C, all of the antibodies are against antigens associated with neoplastic cells. Similarly a reagent could contain antibodies to multiple B cell antigens or antigens associated with reactive cells. A reagent with antibodies to both reactive antigens and neoplastic antigens, however, would be useless because it would be unable to differentiate cells based on the relevant biological state.

Concurrently with the neoplastic panel, the specimen will be investigated using the reactive panel 803. The reactive panel comprises ancillary reagent constructs conjugated to antibodies to HBME-1 and LCA. HBME-1 is an antigen associated with reactive mesothelial cells that bear a morphological resemblance to tumor cells but are not neoplastic. LCA is an antigen expressed by histocytes, which are also appear similar to tumor cells but are not neoplastic.

Unlike the neoplastic panel, when the detection agent is proximal to cells then they are likely not neoplastic. Their presence supports a benign or reactive diagnosis. For example, when the cells appear morphologically normal 807 then the presence of the reagent is further evidence that the cells are not neoplastic and the cells benign 808. If the cells appear atypical, and the reagent is negative 809, then that result supports a reactive diagnosis.

In that sense, the neoplastic and reactive panels work together. Consistent results between the two reinforce the morphologic evaluation of the specimen. For example, if a cell appears atypical and is positive for the neoplastic panel 805 and negative for the reactive panel 809 then it is very likely that the specimen is neoplastic. That specimen should undergo analysis using an ancillary technique 806 like flow cytometry.

Figure 8D:
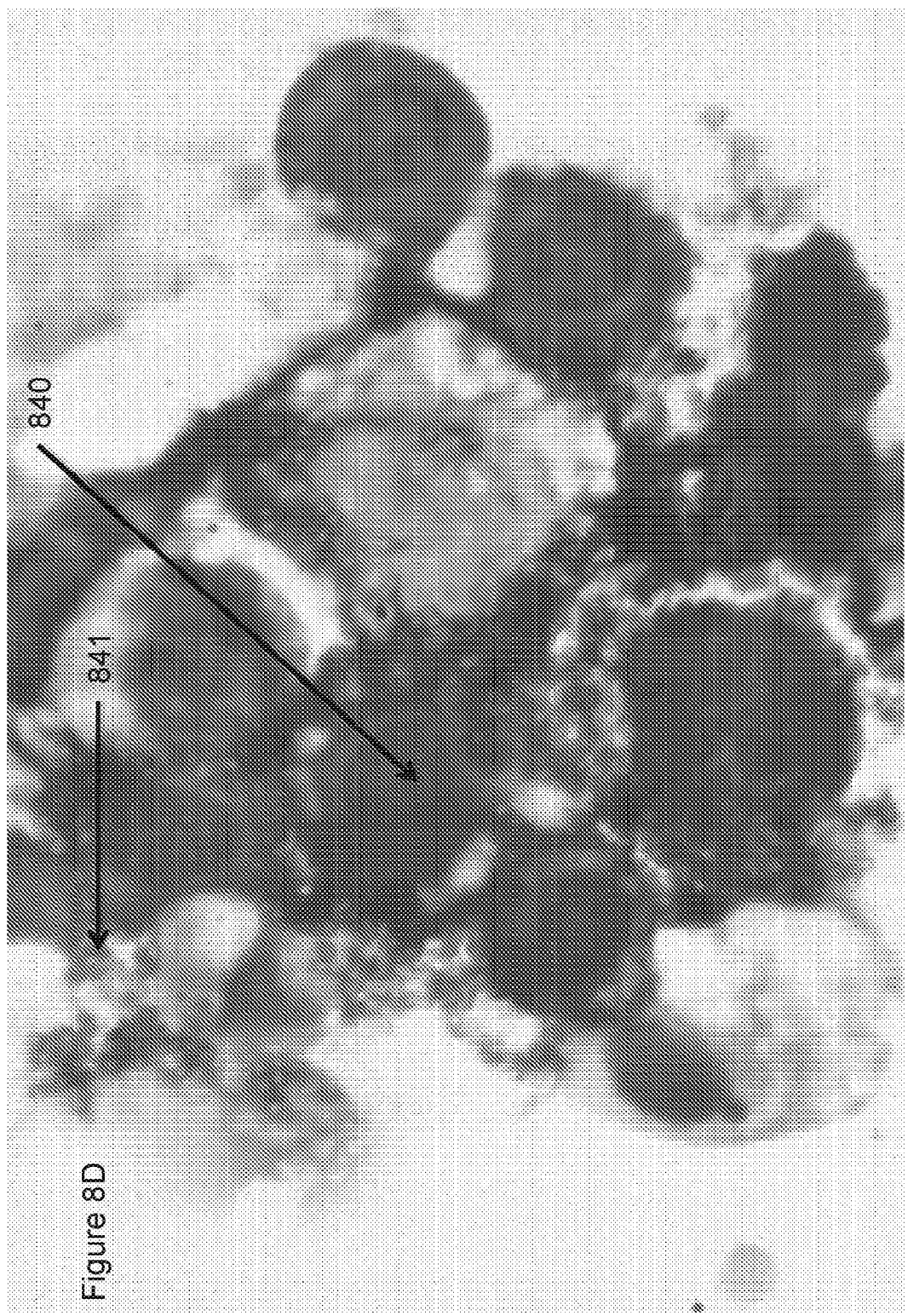
Figure 8E:
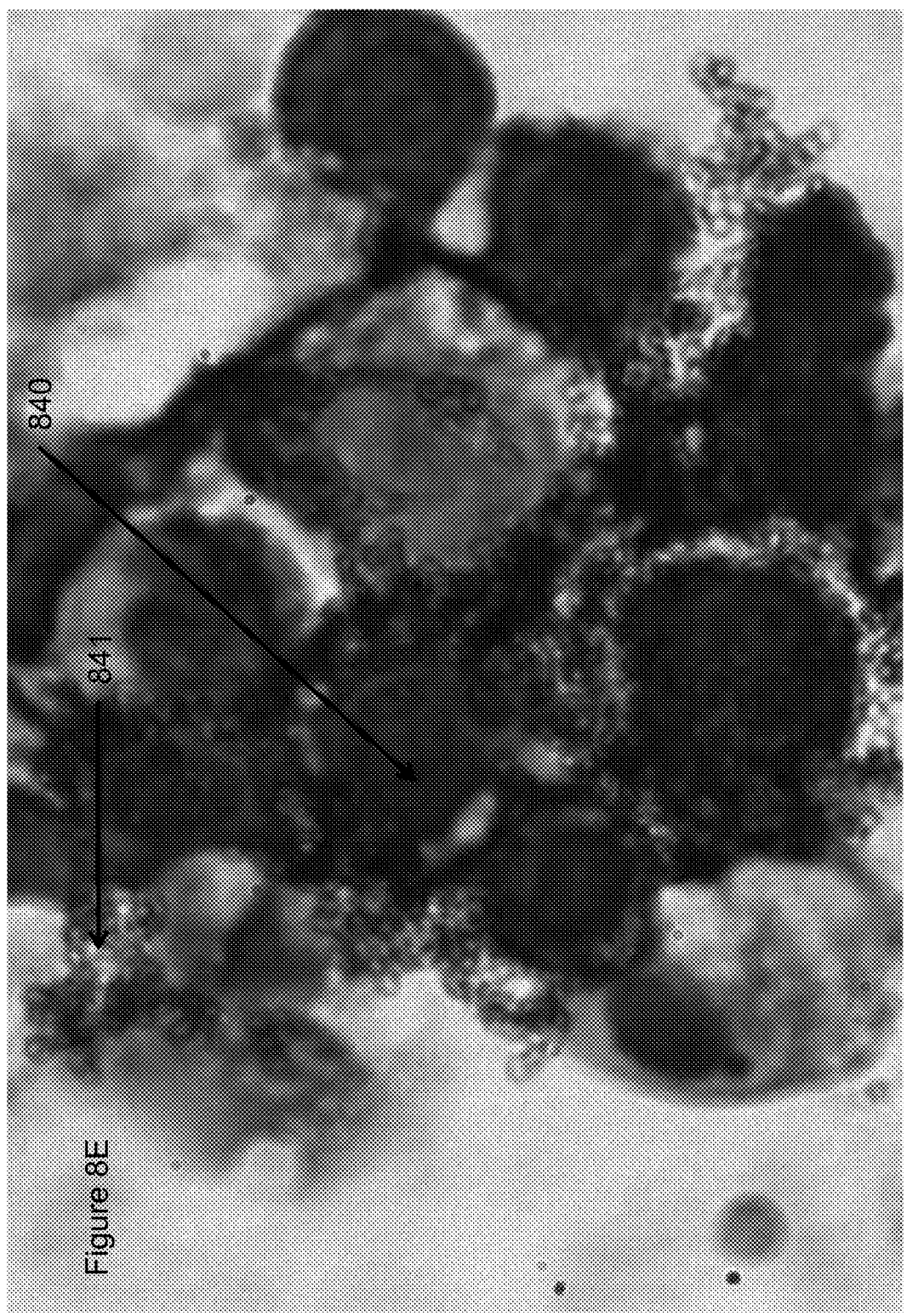

FIG. 8D is a photomicrograph of a specimen evaluated using the reactive panel. The specimen is a pleural fluid, which, in this slide has undergone evaluation with an ancillary reagent construct that is conjugated to an antibody to HBME-1. The detection agent is a Solulink, Nanolink™ 0.8 micron magnetic bead cluster. The specimen was stained with a standard wright stain, rendering the cells, which appear to be mesothelial cells, 840 visible. The detection agents 841, which are proximal to the mesothelial cells, strongly support that the cells are reactive—not neoplastic. FIG. 8E is the same micrograph with the birefringence filter removed. In the micrograph, the detection agents 841 are more visible.

Figure 8F:
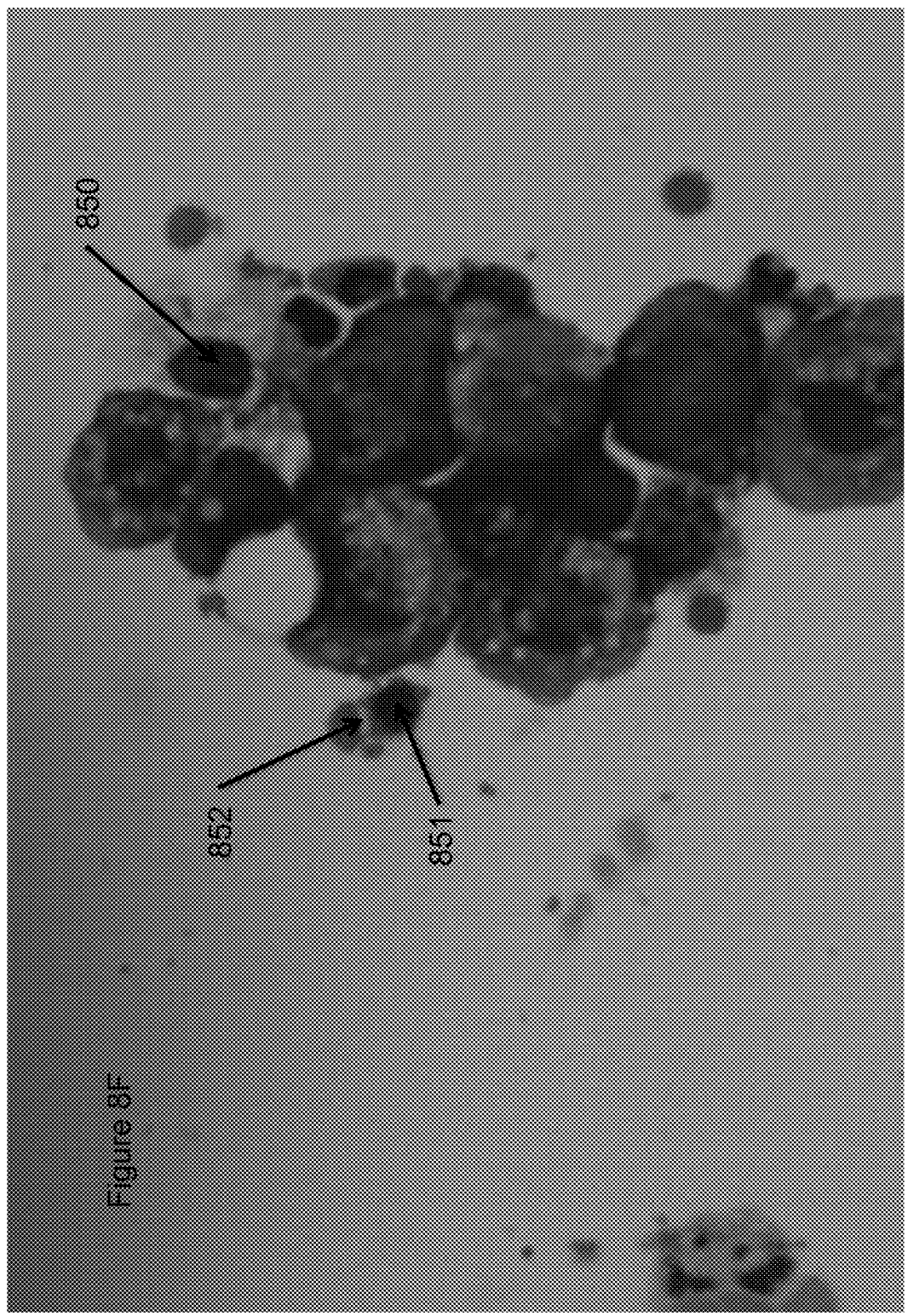
Figure 9:
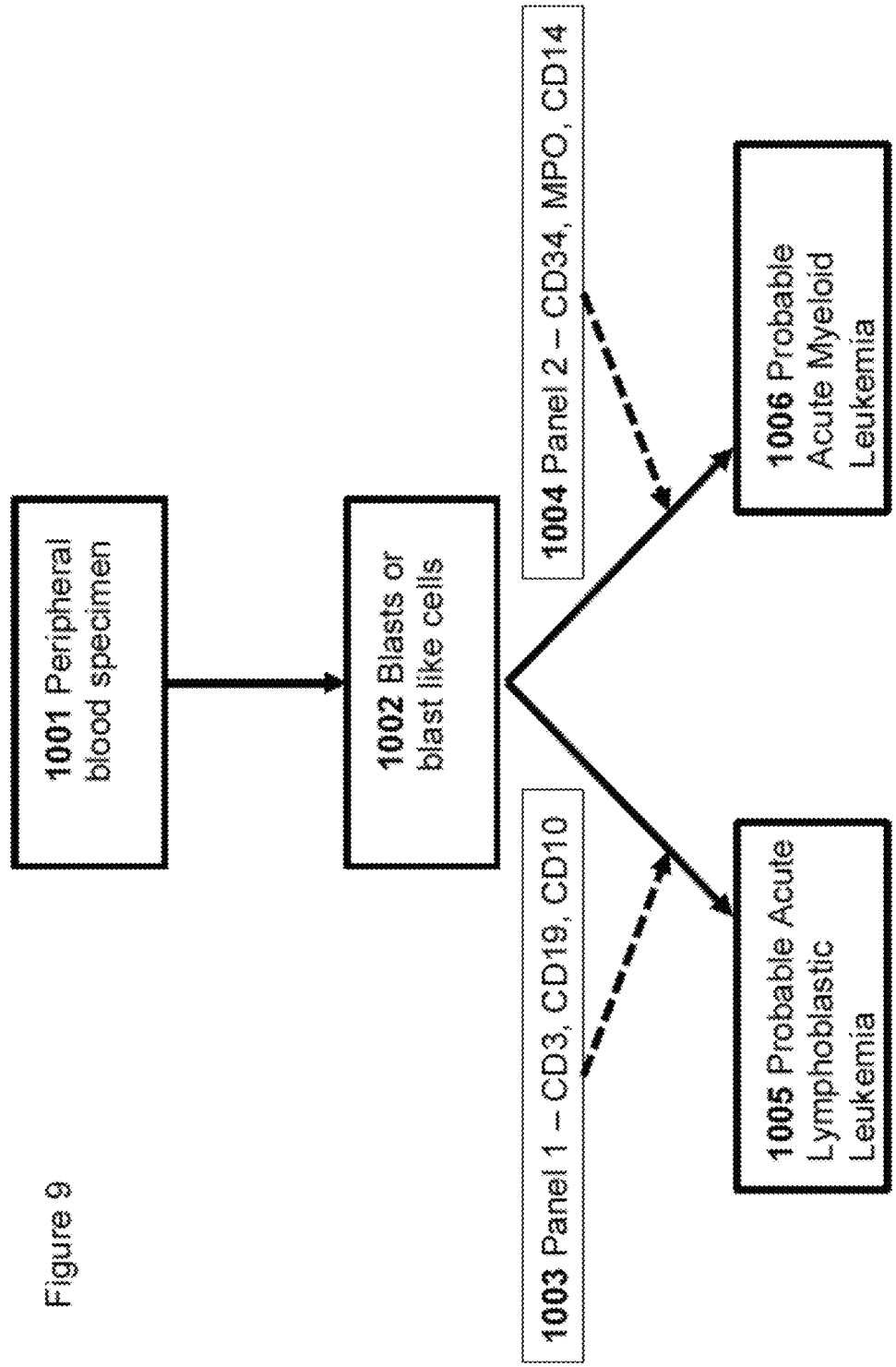
FIG. 9 is a flow chart illustrating the application of an acute leukemia ancillary kit to blood specimens.

FIG. 8F is a photomicrograph of a specimen evaluated using the reactive panel. The specimen is a pleural fluid, which, in this slide, has undergone evaluation with an ancillary reagent construct that is conjugated to an antibody to LCA. The detection agent is a 1 micron Dynabead® paramagnetic microparticle. The specimen was stained with a standard wright stain, rendering both reactive 851 and tumor 850 cells visible.

The detection agents 852, are proximal to the reactive cells 851 but not the tumor cells 850. It would be expected that a specimen, when stained with the neoplastic panel, would produce the opposite result.

The use of the body fluid kit is to assist in the identification of a tumor cell in body fluid specimen. The reagents provide additional information to the pathologist. If, morphologically, a cell is difficult to differentiate between a mesothelial cell or a carcinoma then immunological information is very helpful. If, after exposure to the neoplastic panel, a cell has a detection agent in close proximity to it then the pathologist is likely more confidant to call it a tumor. If it is treated with the reactive panel and a detection agent is present, then it is not.

In aggregate, the panel gives a great deal of information. If a specimen contains borderline cells that are positive for one or more of the reagents in the reactive panel and negative for all the reagents in the neoplastic panel then the pathologist will make a reactive diagnosis with much greater confidence.

Example 3: Acute Leukemia Kit

Pathology is not only used to diagnose the presence or absence of disease but qualify the nature of the disease so as to direct treatment. For example, if a blood specimen contains cells that the pathologist suspects are blasts then it is difficult to distinguish between Acute Lymphoblastic Leukemia (ALL) and Acute Myeloid Leukemia (AML). Currently, such specimens are sent for analysis using ancillary techniques like flow cytometry to determine the presence of antigens associated with ALL or AML.

Figure 10:
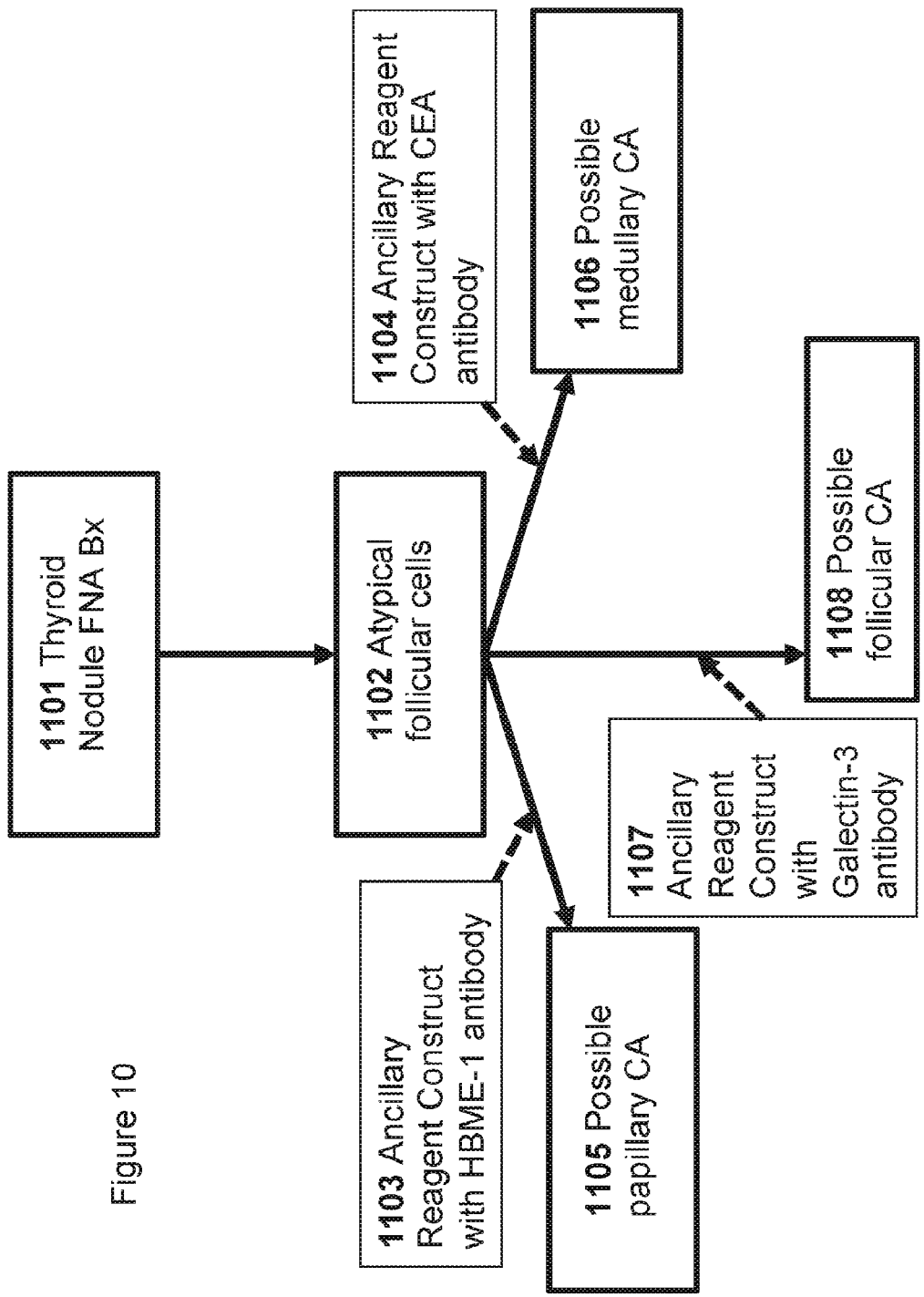
FIG. 10 is a flow chart illustrating the application of the thyroid nodule ancillary kit to single cell suspensions of fine needle biopsy specimens.

In one embodiment, the invention is a ancillary kit that can differentiate between ALL and AML in blood specimens with blasts or suspected blasts. Looking now to FIG. 10, a pathologist evaluates a peripheral blood specimen 1001 to identify if blasts or blast like cells are present 1002. If blasts are present in the specimen then the pathologist utilizes the kit to distinguish between the two.

The kit comprises two panels of ancillary reagent constructs. The first panel 1003 comprises ancillary reagent constructs that are conjugated to antibodies to antigens associated with ALL. The panel can comprise multiple ancillary reagent constructs conjugated to individual antibodies such as CD3, CD19, CD 22 and CD10. Alternatively, the ancillary reagent constructs can comprise single ancillary reagent constructs that are conjugated to one or more antibodies.

After incubating the specimens in the presence of the first panel 1003 the specimens are smeared onto slides and stained using standard stains. The pathologist identifies the blast or blast-like cells previously identified 1002 and then looks to see if the detection agent from one or more of the ancillary reagent constructs in the first panel are proximal to the cell. If the detection agent is proximal to the blast or blast-like cells then the pathologist can diagnose ALL with greater confidence 1005.

The second panel 1004 comprises ancillary reagent constructs that are conjugated to antibodies to antigens associated with AML. The panel can comprise multiple ancillary reagent constructs conjugated to individual antibodies such as CD34. MPO and CD14. Alternatively, the ancillary reagent constructs can comprise single ancillary reagent constructs that are conjugated to one or more antibodies.

After incubating the specimens in the presence of the second panel 1004 the specimens are smeared onto slides and stained using standard stains. The pathologist identifies the blast or blast-like cells previously identified 1002 and then looks to see if the detection agent from one or more of the ancillary reagent constructs in the second panel are proximal to the cell. If the detection agent is proximal to the blast or blast-like cells then the pathologist can diagnose AML with greater confidence 1006.

Example 4: Thyroid Fine Needle Biopsy Kit

When medical examination identifies an irregular nodule on a patients thyroid, cytopathology is one means to establish if the nodule is a papillary carcinoma or if it is a medullary carcinoma. For evaluation using cytopathology the fine needle, guided by ultrasound, takes a section of tissue from the nodule. The tissue is then suspended in liquid by various means well known in the and re-suspended in buffer. The specimen, now existing as cells in a liquid matrix, can be evaluated using standard cytopathology protocols.

In one embodiment, the invention is a ancillary kit that can differentiate between papillary carcinoma or a medullary carcinoma. Looking now to FIG. 11, a preparation of a fine needle biopsy of a thyroid nodule 1101 is evaluated utilizing standard stains for the presence of atypical follicular cells 1102. If atypical cells are present it can be very challenging to distinguish between a papillary carcinoma or a medullary carcinoma.

The specimen is incubated in the presence of an ancillary reagent construct conjugated to an antibody to HBME-1 or CK-19. The specimen that was incubated with the ancillary reagent construct conjugated to HBME-1 is then smeared onto a slide. The pathologist examines the slide in the presence of standard stains and identifies the atypical follicular cells 1102 and then looks to see if the detection agent from the ancillary reagent construct is proximal to the cell. If the detection agent is proximal to the suspected atypical follicular cells then the pathologist can diagnose papillary CA with greater confidence 1106.

The specimen is simultaneously incubated in the presence of an ancillary reagent construct conjugated to an antibody to CEA 1104. The specimen that was incubated with the ancillary reagent construct conjugated to CEA is then smeared onto a slide. The pathologist identifies the atypical follicular cells previously identified 1102 and then looks to see if the detection agent from the ancillary reagent construct is proximal to the cell. If the detection agent is proximal to the suspected atypical follicular cells then the pathologist can diagnose medullary CA with greater confidence 1106.

The specimen is simultaneously incubated in the presence of an ancillary reagent construct conjugated to an antibody to Galectin-3 1107. The specimen that was incubated with the ancillary reagent construct conjugated to CEA is then smeared onto a slide. The pathologist identifies the atypical follicular cells previously identified 1102 and then looks to see if the detection agent from the ancillary reagent construct is proximal to the cell. If the detection agent is proximal to the suspected atypical follicular cells then the pathologist can diagnose follicular CA with greater confidence 1108.

It is to be understood that the invention is defined by the appended claims. Although specific embodiments of the invention have been illustrated and described herein, it is apparent that various modifications may be made by those skilled in the art without departing from the scope and spirit of the disclosure.

I claim:

1. A method for conducting simultaneous immunological and morphological investigation comprising the steps of:
   isolating a pathology specimen from a patient;
   selecting at least one appropriate ancillary reagent construct with an antibody to an antigen expressed on a cell associated with a biological state of interest, the at least one appropriate ancillary reagent construct being visible at microscale under light microscopy and physically stable in the presence of an appropriate standard stain, wherein the at least one appropriate ancillary reagent construct comprises a detection agent, wherein the detection agent is a particle ranging from 0.5 to 5 microns;
   counting the number of cells in the pathology specimen;
   administering an appropriate amount of the at least one appropriate ancillary reagent construct;
   administering the appropriate standard stain;
   identifying, via light microscopy, stained cells with morphology consistent with the biological state of interest; and confirming, simultaneously with identification of the stained cells with morphology consistent with the biological state of interest, the biological state of interest based on the absence or presence of the detection agent proximal to the stained cells with morphology consistent with the biological state of interest and not proximal to the stained cells with morphology inconsistent with the biological state of interest.

2. The method of claim 1, wherein:

the patient pathology specimen is whole blood;

the at least one appropriate ancillary reagent construct is a panel of ancillary reagent constructs having the detection agent conjugated to antibodies against B cell antigens and a panel of ancillary reagent constructs having the detection agent conjugated to antibodies against kappa and lambda light chains; and the biological state is lymphocytosis.

3. The method of claim 2, wherein the B cell antigens are selected from the group consisting of CD 19, CD 20, CD24, CD72, and CD73.

4. The method of claim 1, wherein:

the patient pathology specimen is a body fluid;

the at least one appropriate ancillary reagent construct is a neoplastic panel of ancillary reagent constructs and a reactive panel of ancillary reagent constructs; and the biological state is cancer.

5. The method of claim 4, wherein the neoplastic panel comprises ancillary reagent constructs having the detection agent conjugated to antibodies to antigens selected from the group consisting of EPCAM, CEA, CD15, Berep4, ecad, and EMA.

6. The method of claim 4, wherein the neoplastic panel is a single ancillary reagent construct having the detection agent conjugated to antibodies to both EPCAM and CEA.

7. The method of claim 6, wherein the ratio of EPCAM to CEA on the ancillary reagent construct is 5 to 2.

* * * * *